(12) United States Patent
Shieh et al.

(10) Patent No.: US 11,952,619 B2
(45) Date of Patent: Apr. 9, 2024

(54) ARRAYS WITH QUALITY CONTROL TRACERS

(71) Applicant: ILLUMINA, INC., San Diego, CA (US)

(72) Inventors: Peyton Shieh, San Diego, CA (US); John M. Beierle, Carlsbad, CA (US); Michael S. Graige, Cardiff by the Sea, CA (US); Alexander Fuhrmann, San Diego, CA (US); Randall Smith, San Marcos, CA (US); Wei Wei, San Diego, CA (US); Naiqian Zhan, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 662 days.

(21) Appl. No.: 16/868,308

(22) Filed: May 6, 2020

(65) Prior Publication Data

US 2020/0340046 A1 Oct. 29, 2020

Related U.S. Application Data

(62) Division of application No. 15/848,717, filed on Dec. 20, 2017, now abandoned.

(60) Provisional application No. 62/438,284, filed on Dec. 22, 2016.

(51) Int. Cl.
*C12Q 1/6837* (2018.01)

(52) U.S. Cl.
CPC .................................. *C12Q 1/6837* (2013.01)

(58) Field of Classification Search
None
See application file for complete search history.

(56) References Cited

U.S. PATENT DOCUMENTS

| 6,040,138 A | 3/2000 | Lockhart et al. |
| 7,057,026 B2 | 6/2006 | Barnes et al. |
| 7,211,414 B2 | 5/2007 | Hardin et al. |
| 7,315,019 B2 | 1/2008 | Turner et al. |

(Continued)

FOREIGN PATENT DOCUMENTS

| WO | WO 91/06678 | 5/1991 |
| WO | WO 2000/031148 | 6/2000 |

(Continued)

OTHER PUBLICATIONS

The definition of "orthogona sequence" provided by stackexchange. com [retrieved on Jun. 5, 2023]. Retrieved from the Internet: <URL: https://bioinformatics.stackexchange.com/questions/10623/what-are-orthogonal-dna sequences#:~:text=Orthogonal%20DNA%20sequences%20are%20the,of%20binding%20with%20other%20probes.>.*

(Continued)

*Primary Examiner* — Robert T. Crow
(74) *Attorney, Agent, or Firm* — Dierker & Kavanaugh, P.C.

(57) ABSTRACT

An array includes a support including a plurality of discrete wells, a gel material positioned in each of the plurality of discrete wells, and a quality control tracer grafted to the gel material in each of the plurality of discrete wells. The quality control tracer comprises (a) a cleavable nucleotide sequence comprising a cleavage site and (b) a detectable label; and in some aspects, is a cleavable nucleotide sequence with a detectable label and a non-reactive nucleotide sequence or a primer nucleotide sequence.

7 Claims, 13 Drawing Sheets

Specification includes a Sequence Listing.

(56) References Cited

U.S. PATENT DOCUMENTS

| | | |
|---|---|---|
| 7,329,492 B2 | 2/2008 | Hardin et al. |
| 7,405,281 B2 | 7/2008 | Xu et al. |
| 8,778,848 B2 | 7/2014 | Lin et al. |
| 8,778,849 B2 | 7/2014 | Bowen et al. |
| 9,012,022 B2 | 4/2015 | George et al. |
| 9,079,148 B2 | 7/2015 | Rigatti et al. |
| 2003/0215801 A1 | 11/2003 | Pieken et al. |
| 2006/0019267 A1* | 1/2006 | Quake ............... C12Q 1/68 435/6.12 |
| 2007/0172852 A1 | 7/2007 | Zimmerling |
| 2008/0108082 A1 | 5/2008 | Rank et al. |
| 2010/0129810 A1 | 5/2010 | Greiner et al. |
| 2011/0059865 A1 | 3/2011 | Smith et al. |
| 2013/0045872 A1 | 2/2013 | Zhou et al. |
| 2013/0244237 A1 | 9/2013 | Vaisvila et al. |
| 2014/0079923 A1 | 3/2014 | George et al. |
| 2014/0200158 A1 | 7/2014 | Bowen et al. |
| 2014/0243224 A1 | 8/2014 | Barnard et al. |
| 2014/0329723 A1 | 11/2014 | Lin et al. |
| 2015/0005200 A1 | 1/2015 | Hindson et al. |
| 2015/0005447 A1 | 1/2015 | Berti et al. |
| 2015/0051117 A1* | 2/2015 | Church ............ C12N 15/1065 506/41 |
| 2015/0118685 A1 | 4/2015 | Clark et al. |
| 2015/0329891 A1* | 11/2015 | Tan .................. C12P 19/34 435/320.1 |

FOREIGN PATENT DOCUMENTS

| | | |
|---|---|---|
| WO | WO 2001/001143 | 1/2001 |
| WO | WO 2003/014392 | 2/2003 |
| WO | WO 04/018497 | 3/2004 |
| WO | WO 2004/106890 | 12/2004 |
| WO | WO 07/123744 | 11/2007 |
| WO | WO 2013/063382 | 5/2013 |
| WO | WO 2014/133905 | 9/2014 |
| WO | 2016/075204 A1 | 5/2016 |

OTHER PUBLICATIONS

Butler, et al., "Quality control of PCR primers used in multiplex STR amplification reactions", Forensic Science International 119 (2001) pp. 87-96.

International Search Report and Written Opinion for International Application No. PCT/US2017/067575 dated Apr. 16, 2018, 19 pages.

Hessner, et al. "Utilization of a Labeled Tracking Oligonucleotide for Visualization and Quality Control of Spotted 70-mer Arrays", BMC Genomics, 5:12, 2004, 11 pages.

Bentley et al., "Accurate whole human genome sequencing using reversible terminator chemistry", Nature, 2008, 456:53-59, Macmillan Publishers Limited.

* cited by examiner

ARRAYS WITH QUALITY CONTROL TRACERS

CROSS-REFERENCE TO RELATED APPLICATIONS

This application is a divisional of U.S. patent application Ser. No. 15/848,717, filed Dec. 20, 2017, which itself claims the benefit of U.S. Provisional Application Ser. No. 62/438,284, filed Dec. 22, 2016, the contents of each of which is incorporated by reference herein in its entirety.
REFERENCE TO SEQUENCE LISTING
The Sequence Listing submitted herewith via EFS-Web is hereby incorporated by reference in its entirety. The name of the file is ILI104C_IP-1477A-US_Sequence_Listing_3_ST25.txt, the size of the file is 7,380 bytes, and the date of creation of the file is Jul. 15, 2020.

BACKGROUND

Biological arrays are among a wide range of tools used to detect, analyze, and/or sequence molecules, including deoxyribonucleic acid (DNA) and ribonucleic acid (RNA). In these applications, the arrays are engineered to include nucleic acid sequences useful as sequencing or amplification primers or as probes for nucleotide sequences present in genes in humans and other organisms. Beyond these applications, biological arrays may be used for the detection and evaluation of a wide range of molecules, families of molecules, genetic expression levels, single nucleotide polymorphisms, and genotyping.

In general, genetic sequencing involves determining the order of nucleotides or nucleic acids in a length of genetic material, such as a fragment of DNA or RNA. Increasingly longer sequences of base pairs are being analyzed, and the resulting sequence information may be used in various bioinformatics methods to logically fit fragments together so as to reliably determine the sequence of extensive lengths of genetic material from which the fragments were derived. Automated, computer-based examination of characteristic fragments have been developed, and have been used in genome mapping, identification of genes and their function, evaluation of risks of certain conditions and disease states, and so forth. In certain applications, for example, modified target nucleic acids are hybridized to sequencing or amplification primers on the surface of an array, amplified, and their genetic sequences determined.

In other examples, individual DNA and RNA probes may be attached at small locations in a geometric grid (or randomly) on an array support. A test sample, e.g., from a known person or organism, may be exposed to the grid, such that complementary fragments hybridize to the probes at the individual sites in the array. The array can then be examined by scanning specific frequencies of light over the sites to identify which fragments are present in the sample, by fluorescence of the sites at which the fragments hybridized.

Proper functionality and reproducibility of the nucleic acid-functionalized array depends on consistent display of the nucleic acid sequences bound thereto. The present application is directed to quality control compositions, arrays, and methods for ensuring consistent deposition of nucleic acid sequences on the array surface and retention of the sequences following any subsequent manufacturing and storage of the arrays.

SUMMARY

In certain aspects, the present disclosure is directed to an array that includes a support comprising a plurality of discrete wells, a gel material positioned in each of the plurality of discrete wells, and a quality control tracer grafted to the gel material in each of the plurality of discrete wells. In some embodiments, the quality control tracer grafted to the gel material comprises (a) a cleavable nucleotide sequence comprising a cleavage site and (b) a detectable label. In some embodiments, the quality control tracer is grafted to the gel material at a first end of the tracer. In some embodiments, the cleavable nucleotide sequence comprises a grafted region with a first end and a second end, where the first end is grafted to the gel material and the second end is linked to a cleavable region that is linked to the detectable label and comprises the cleavage site. In some embodiments, the cleavable nucleotide sequence comprises a non-reactive nucleotide sequence, and in some instances, the grafted region comprises the non-reactive nucleotide sequence. In other embodiments, the cleavable nucleotide sequence comprises a primer nucleotide sequence, and in some instances, the grafted region comprises the primer nucleotide sequence.

In some embodiments, the detectable label is linked to the quality control tracer or cleavable nucleotide sequence at the cleavage site. In other embodiments, the detectable label is linked to the quality control tracer or cleavable nucleotide sequence at a position that is distal to the cleavage site and the grafted first end (e.g., support—grafted first end of tracer—cleavage site of tracer—detectable label on tracer), and in further embodiments, that position is at the 3' end of the cleavable nucleotide sequence. In some embodiments, the detectable label is attached at or near the 3' end of the cleavable nucleotide sequence. In some embodiments, the cleavable nucleotide sequence is grafted to the gel material at its 5' end. In some embodiments, the detectable label is cleavable by reaction of the quality control tracer with an exonuclease. In other embodiments, the detectable label is cleavable by reaction of the quality control tracer with a glycosylase and an endonuclease.

In some embodiments, the cleavage site is a cleavable nucleobase. In some embodiments, the cleavable nucleobase is an enzymatically cleavable nucleobase. In some embodiments, the enzymatically cleavable nucleobase comprises an excision site. In some embodiments, the cleavable nucleobase is susceptible to cleavage by reaction with a glycosylase and an endonuclease, or with an exonuclease. In some embodiments, the cleavage site comprises a chemically cleavable linker. In some embodiments, the chemically cleavable linker comprises a vicinal diol, a disulfide, a silane, an azobenzene, a photocleavable group, or an azido.

In some embodiments, the detectable label is a fluorescent label.

In some embodiments, the quality control tracer comprises (a) a cleavable nucleotide sequence tagged, at its 3' end, with a fluorescent label or (b) a non-reactive nucleotide sequence comprising a cleavable nucleobase with a fluorescent label attached thereto. In some aspects, the cleavable nucleotide sequence comprises a primer nucleotide sequence. In some aspects, the array with quality control tracer further comprises an unlabeled primer grafted to the gel material in each of the plurality of discrete wells, wherein the primer comprises a primer nucleotide sequence. Such arrays are contemplated for use in any of the methods described herein.

In some embodiments, the quality control tracer does not comprise a primer nucleotide sequence, and the array further comprises a separate unlabeled primer comprising a primer nucleotide sequence grafted to the gel material in each of the plurality of discrete wells. In some embodiments, the quality control tracer and the unlabeled primer (and thus, the primer nucleotide sequence) are present on the gel material in a predetermined ratio.

The present application is directed to a method of determining the density and/or distribution of a grafted primer nucleotide sequence comprising: providing a support comprising a plurality of discrete wells and a gel material positioned in each of the plurality of discrete wells and a quality control tracer and the primer nucleotide sequence grafted to the gel material in each of the plurality of discrete wells; wherein the quality control tracer comprises (a) a cleavable nucleotide sequence comprising a cleavage site and (b) a detectable label; and detecting a signal from the detectable label; determining the density and/or distribution of the quality control tracer based at least in part on the signal from the detectable label; and determining the density and/or distribution of the grafted primer nucleotide sequence based at least in part on the determined density and/or distribution of the quality control tracer. In some embodiments, the method further comprises grafting the quality control tracer to the gel material. In some aspects, the quality control tracer comprises the primer nucleotide sequence. In other aspects, the quality control tracer comprises a non-reactive nucleotide sequence (and no primer nucleotide sequence), and the primer nucleotide sequence is grafted to the gel material, either before or at the same time as the grafting of the quality control tracer, and prior to the detecting step. In other embodiments, the quality control tracer comprises the primer nucleotide sequence, such that grafting of the quality control tracer serves to graft both the tracer and the primer nucleotide sequence to the gel material. In some embodiments, the quality control tracer and the primer nucleotide sequence are grafted to the gel material in a predetermined ratio and the determining of the density and/or distribution of the primer nucleotide sequence is based on the detected signal and the predetermined ratio. In some embodiments, the method further comprises removing the detectable label from the quality control tracer by a cleavage reaction at the cleavage site. In some instances, the removing is accomplished by enzymatic cleavage or chemical cleavage. In some instances, the removing is done by reaction at the cleavage site with a glycosylase and an endonuclease or with an exonuclease. In other instances, the removing is accomplished by chemical reaction of a linker molecule attaching the cleavable nucleotide sequence to the detectable label.

In an example of the methods disclosed herein, a quality control tracer is grafted to a gel material in a well on a support. The quality control tracer is detected, for example, using fluorescence where the detectable label is a fluorescent label, and, based at least in part on the detected signal or fluorescence, a density, or a distribution, or the density and the distribution, of a primer nucleotide sequence grafted to the gel material is/are determined. In some aspects, the method comprises grafting a quality control tracer to a gel material in a well on a support, detecting the quality control tracer using fluorescence, and, based at least in part on the fluorescence, determining a density, or a distribution, or the density and the distribution, of a primer nucleotide sequence grafted to the gel material. In some aspects, the method further comprises cleaving the detectable label from the quality control tracer at the cleavage site.

In another aspect, the present disclosure is directed to a method of co-grafting a quality control tracer and a primer nucleotide sequence to an array, comprising: combining a quality control tracer and a primer nucleotide sequence at a predetermined ratio to form a grafting mix; exposing the grafting mix to a gel material in a well on a support; and incubating the grafting mix and the gel material, thereby co-grafting the quality control tracer and the primer nucleotide sequence to the gel material. In some aspects, the quality control tracer is a cleavable nucleotide sequence tagged, at its 3' end, with a fluorescent label or a non-reactive nucleotide sequence with a fluorescent label attached to a cleavable nucleobase. In some aspects, the method further comprises detecting the grafted quality control tracer by detecting a signal from the detectable label; and based at least in part on the detected signal and the predetermined ratio, determining a density, or a distribution, or the density and the distribution, of the primer nucleotide sequence grafted to the gel material. In some aspects, the grafted quality control tracer is detected using fluorescence, and based at least in part on the fluorescence and the predetermined ratio, a density, or a distribution, or the density and the distribution, of the primer nucleotide sequence grafted to the gel material is/are determined. In further aspects, the support comprising the co-grafted gel material is then used in a method of determining the density and/or distribution of a grafted primer nucleotide sequence as described herein. In other aspects, the method further comprises removing the detectable label from the cleavable nucleotide sequence via enzymatic cleavage or chemical cleavage at the cleavage site as described herein.

In another aspect, the present disclosure is directed to a method of grafting a quality control tracer to an array, comprising grafting a quality control tracer to a gel material in a well on a support, wherein the quality control tracer comprises a cleavable nucleotide sequence comprising a cleavage site and a detectable label, wherein the cleavable nucleotide sequence comprises a grafted region with a first end and a second end, where the first end is grafted to the gel material and the second end is linked to a cleavable region that is linked to the detectable label and comprises the cleavage site. In some aspects, the quality control tracer comprises a primer nucleotide sequence in the grafted region, i.e., between the grafted first end of the quality control tracer grafted region and the cleavage site. With this arrangement, cleavage at the cleavage site leaves an unlabeled primer sequence grafted to the gel material. In some aspects, the method further comprises cleaving the quality control tracer at the cleavage site, thereby providing a primer sequence that lacks the detectable label grafted to the gel material, according to the cleavage methods described herein.

In another aspect, the present invention is directed to a grafting mix comprising a primer comprising a primer nucleotide sequence and a quality control tracer, wherein the primer and the quality control tracer are present in the mix in a predetermined ratio.

BRIEF DESCIRPTION OF THE DRAWINGS

Features and advantages of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

Figure 7A:
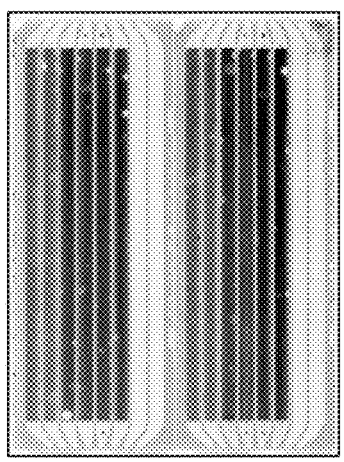
Figure 7B:
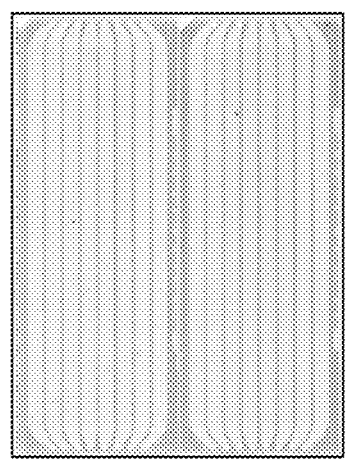
Figure 8A:
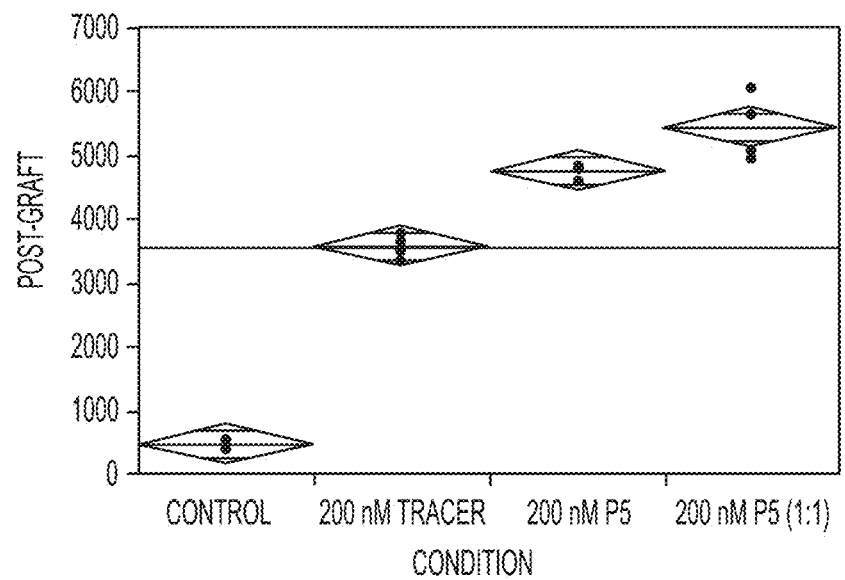
Figure 8B:
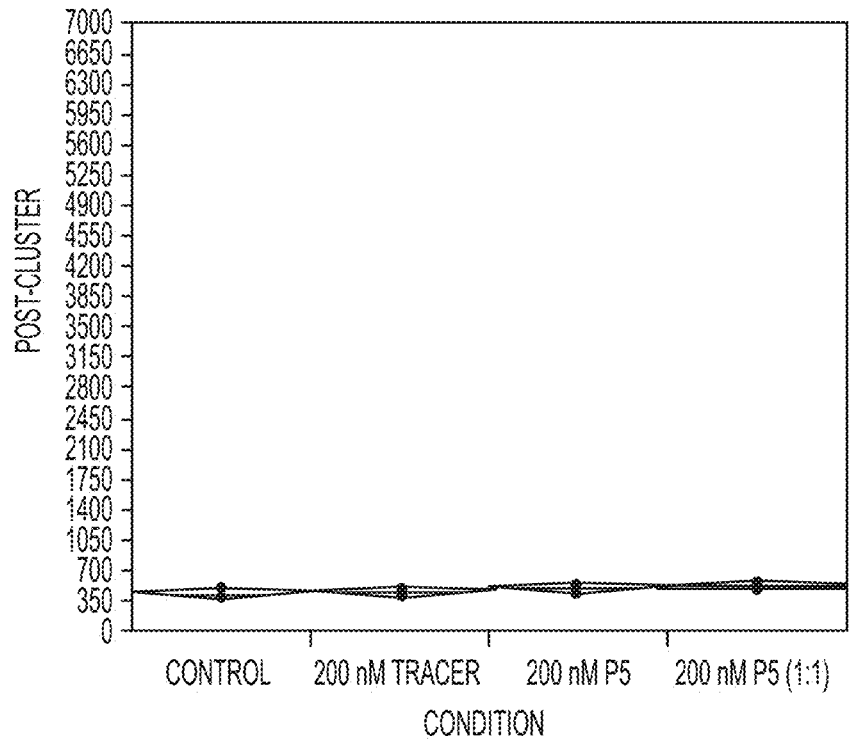
Figure 9A:
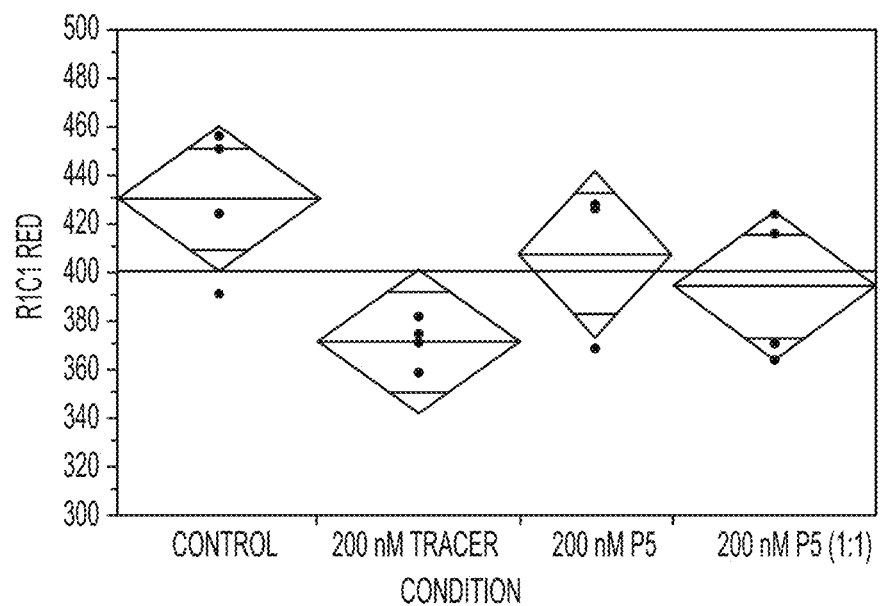
Figure 9B:
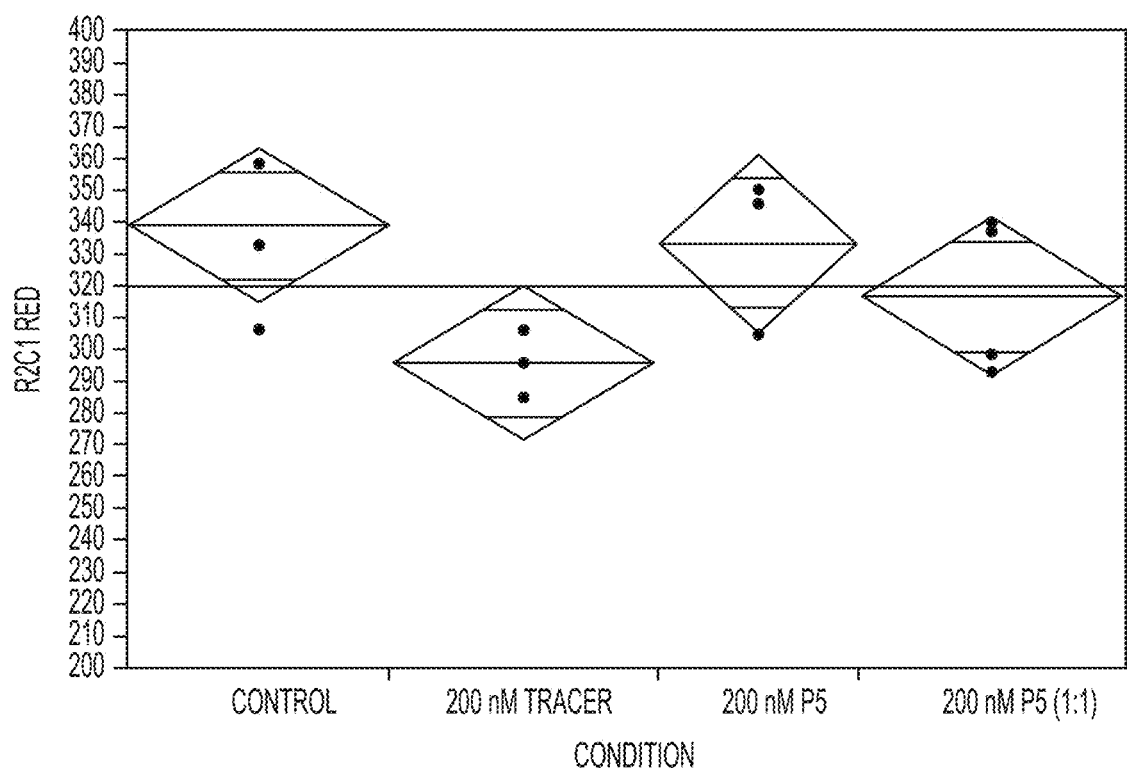
Figure 10A:
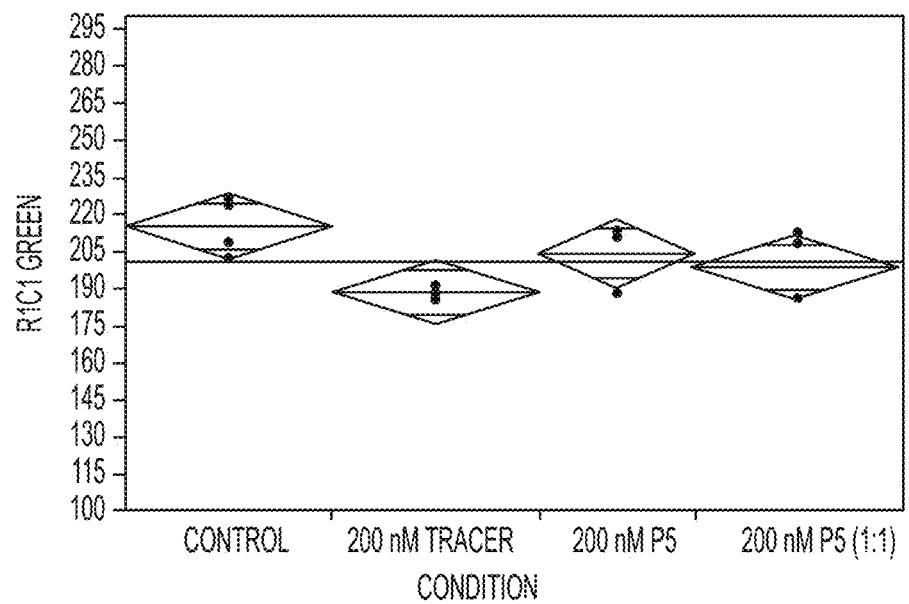
Figure 10B:
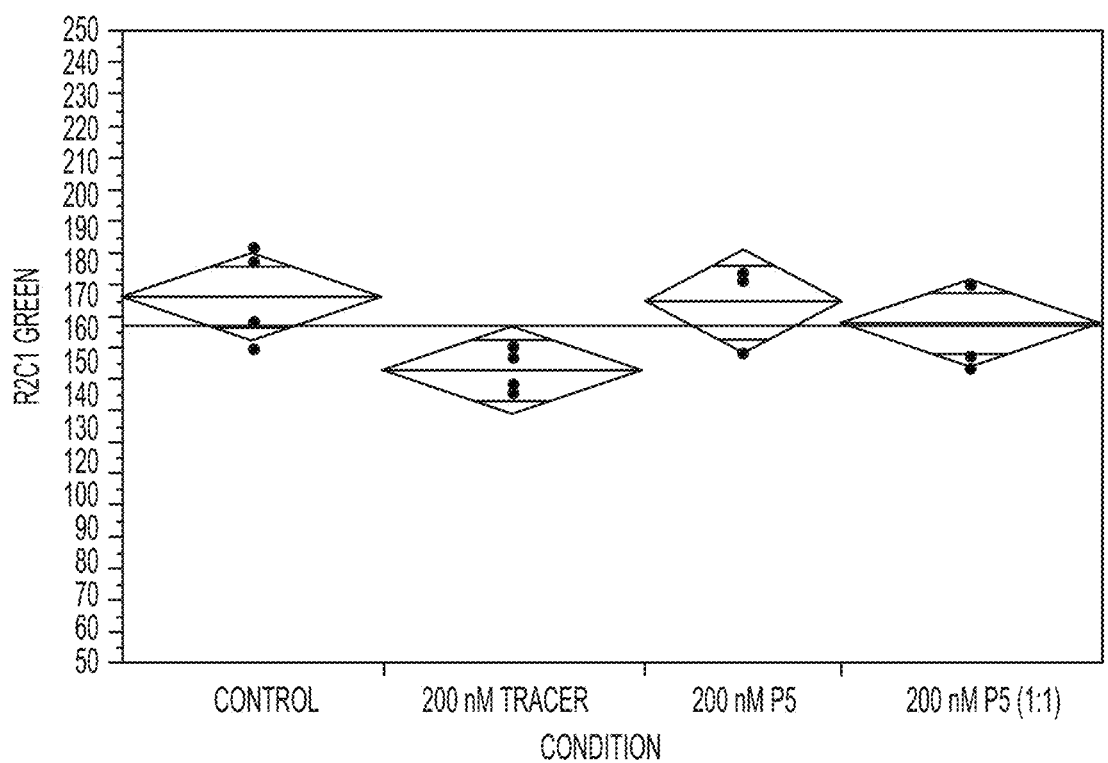
Figure 11A:
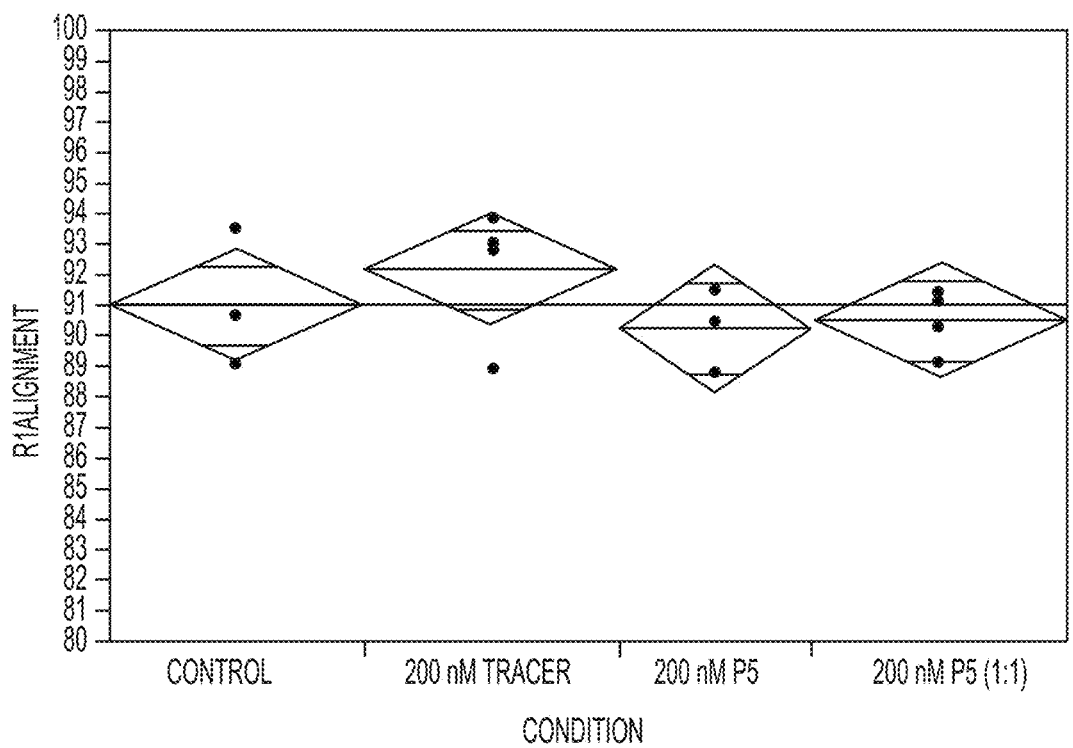
Figure 11B:
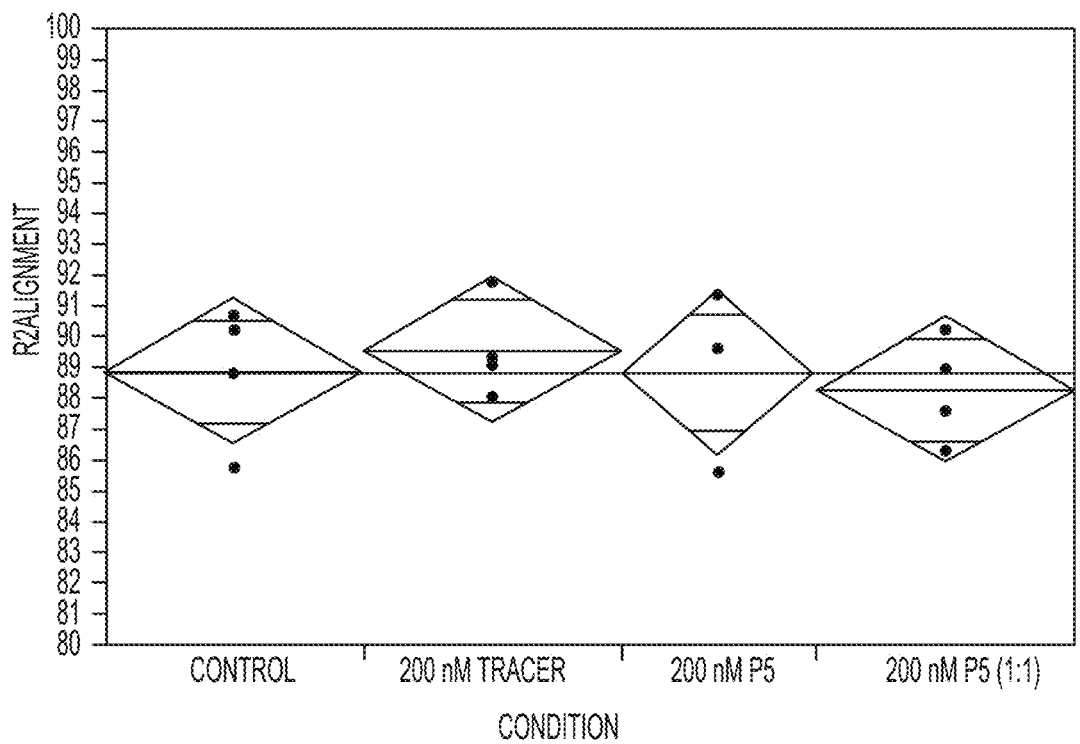
Figure 12A:
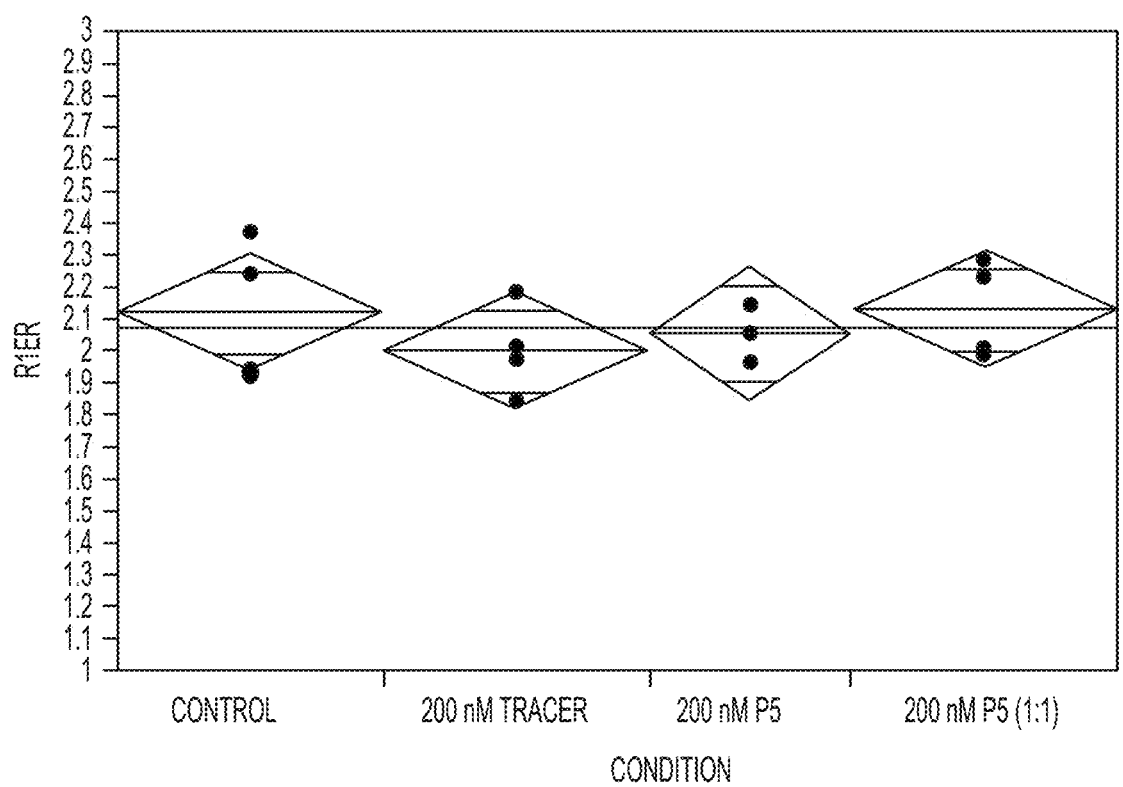
Figure 12B:
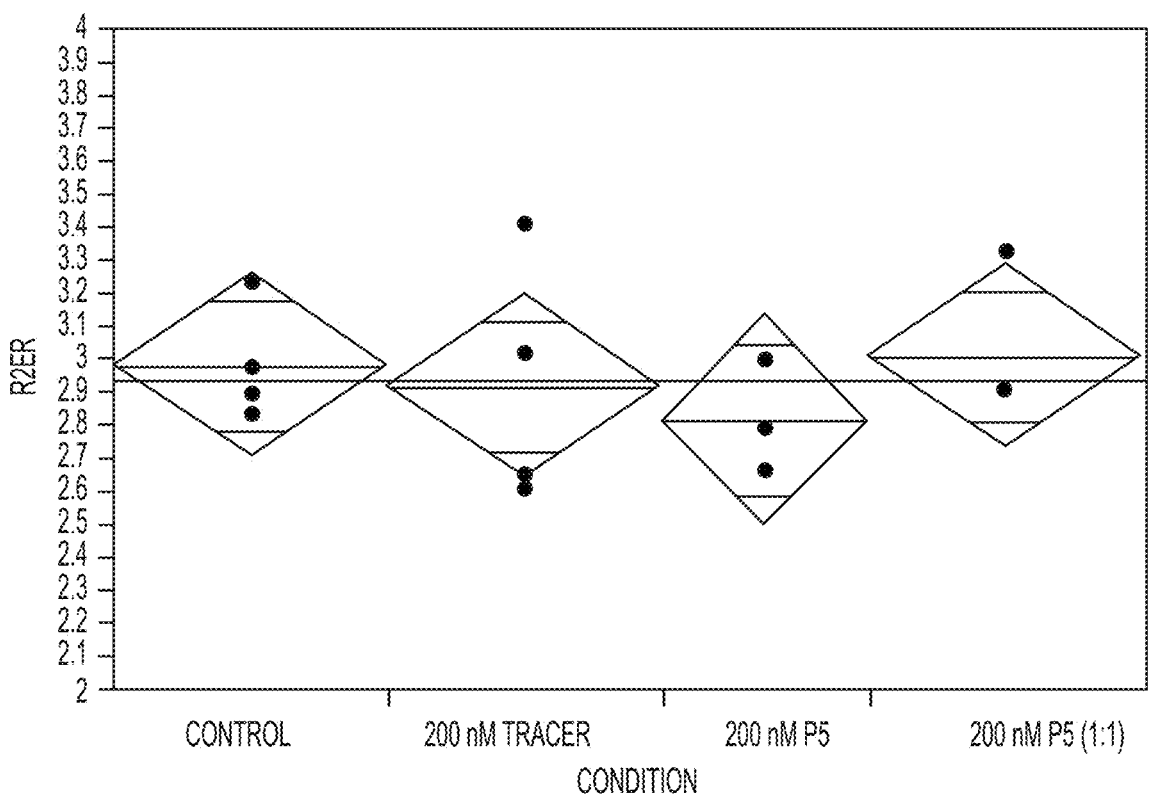

FIGS. 7A and 7B respectively illustrate an initial fluorescence image (before cluster generation) and a post-clustering fluorescence image (after cluster generation) of flow cells grafted with an example of the quality control tracer disclosed herein;

FIGS. 8A and 8B show a plot of quality control tracer fluorescence post-grafting and a plot of quality control tracer fluorescence post-clustering, respectively, for the grafted flow cells of FIGS. 7A and 7B;

FIGS. 9A and 9B show a plot of the read 1 (R1) fluorescence intensity and a plot of the read 2 (R2) fluorescence intensities, respectively, for the red channel after one sequencing cycle (C1) using the grafted flow cells of FIGS. 7A and 7B;

FIGS. 10A and 10B show a plot of the read 1 (R1) fluorescence intensity and a plot of the read 2 (R2) fluorescence intensities, respectively, for the green channel after one sequencing cycle (C1) using the grafted flow cells of FIGS. 7A and 7B;

FIGS. 11A and 11B show a plot of read 1 (R1) sequence alignment and a plot of read 2 (R2) sequence alignment, respectively, to a reference genome for the grafted flow cells of FIGS. 7A and 7B; and FIGS. 12A and 12B respectively show a plot of read 1 (R1) sequencing error rates and plot of read 2 (R2) sequencing error rates for the grafted flow cells of FIGS. 7A and 7B.

DETAILED DESCRIPTION

It is to be understood that terms used herein will take on their ordinary meaning in the relevant art unless specified otherwise. Several terms used herein and their meanings are set forth below.

The singular forms "a", "an", and "the" include plural referents unless the context clearly dictates otherwise.

As used herein, "alkyl" refers to a straight or branched hydrocarbon chain that is fully saturated (i.e., contains no double or triple bonds). The alkyl group may have 1 to 20 carbon atoms. Example alkyl groups include methyl, ethyl, propyl, isopropyl, butyl, isobutyl, tertiary butyl, pentyl, hexyl, and the like. As an example, the designation "C1-4 alkyl" indicates that there are one to four carbon atoms in the alkyl chain, i.e., the alkyl chain is selected from the group consisting of methyl, ethyl, propyl, iso-propyl, n-butyl, isobutyl, sec-butyl, and t-butyl.

The alkyl may be substituted with a halide or halogen, which means any one of the radio-stable atoms of column 7 of the Periodic Table of the Elements, e.g., fluorine, chlorine, bromine, or iodine. This group is referred to as an "alkyl halide".

As used herein, "alkenyl" or "alkene" refers to a straight or branched hydrocarbon chain containing one or more double bonds. The alkenyl group may have 2 to 20 carbon atoms. Example alkenyl groups include ethenyl, propenyl, butenyl, pentenyl, hexenyl, and the like. The alkenyl group may be designated as, for example, "C2-4 alkenyl," which indicates that there are two to four carbon atoms in the alkenyl chain.

As used herein, "alkynyl" or "alkyne" refers to a straight or branched hydrocarbon chain containing one or more triple bonds. The alkyne group may have 2 to 20 carbon atoms. The alkyne group may be designated, for example, as "C2-4 alkynyl," which indicates that there are two to four carbon atoms in the alkyne chain.

An "amido" functional group refers to

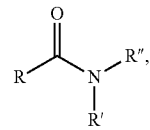

where R is any group that can attach to a fluorescent lable, R' is H, and R" is any group that can attached to a nucleotide sequence.

An "amino" functional group refers to an —$NR_aR_b$ group, where $R_a$ and $R_b$ are each independently selected from hydrogen, C1-6 alkyl, C2-6 alkenyl, C2-6 alkynyl, C3-7 carbocyclyl, C6-10 aryl, 5-10 membered heteroaryl, and 5-10 membered heterocyclyl, as defined herein).

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, which may be designated as C6-18. Examples of aryl groups include phenyl, naphthyl, azulenyl, and anthracenyl.

An "azide" or "azido" functional group refers to —$N_3$.

As used herein, the term "attached" refers to the state of two things being joined, fastened, adhered, connected or bound to each other. For example, a nucleic acid can be attached to a material, such as the gel material, by a covalent or non-covalent bond. A covalent bond is characterized by the sharing of pairs of electrons between atoms. A non-covalent bond is a chemical bond that does not involve the sharing of pairs of electrons and can include, for example, hydrogen bonds, ionic bonds, van der Waals forces, hydrophilic interactions and hydrophobic interactions.

As used herein, "carbocyclyl" means. When the carbocyclyl is a ring system, two or more rings may be joined together in a fused, bridged or spiro-connected fashion. Carbocyclyls may have any degree of saturation, provided that at least one ring in a ring system is not aromatic. Thus, carbocyclyls include cycloalkyls, cycloalkenyls, and cycloalkynyls. The carbocyclyl group may have 3 to 20 carbon atoms (i.e., C3-20).

As used herein, "cycloalkenyl" or "cycloalkane" means a carbocyclyl ring or ring system having at least one double bond, wherein no ring in the ring system is aromatic. Examples include cyclohexenyl or cyclohexene and norbornene or norbornyl

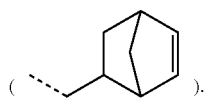

Also as used herein, "heterocycloalkenyl" or "heterocycloalkene" means a carbocyclyl ring or ring system with at least one heteroatom in ring backbone, having at least one double bond, wherein no ring in the ring system is aromatic.

As used herein, "cycloalkynyl" or "cycloalkyne" means a carbocyclyl ring or ring system having at least one triple bond, wherein no ring in the ring system is aromatic. An example is cyclooctyne

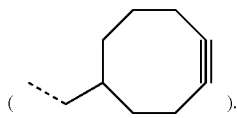

Another example is bicyclononyne (i.e., a bicyclic ring system, such as

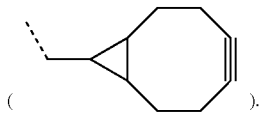

Also as used herein, "heterocycloalkynyl" or "heterocycloalkyne" means a carbocyclyl ring or ring system with at least one heteroatom in ring backbone, having at least one triple bond, wherein no ring in the ring system is aromatic.

The term "chemical cleavage," as used herein, refers to a chemical reaction that removes the quality control tracer or a portion thereof from a support.

As used herein, the term "cleavable nucleotide sequence" refers to a single stranded nucleic acid sequence that can be broken at an excision site or at a linker molecule.

The term "each," when used in reference to a collection of items, is intended to identify an individual item in the collection, but does not necessarily refer to every item in the collection. Exceptions can occur if explicit disclosure or context clearly dictates otherwise.

As used herein, the term "enzymatic cleavage" refers to a process that utilizes an endonuclease or an exonuclease to remove the quality control tracer or a portion thereof from the support.

The term "excision site," as used herein, refers to a nucleotide or a base of a nucleotide (i.e., nucleobase) that is targeted by an enzyme. A quality control tracer or a portion thereof can be cleaved at the excision site. Such cleavage may involve a single enzymatic step or multiple enzymatic steps (e.g., base modification or excision followed by cleavage).

The term "fluorescent label," as used herein, refers to a fluorophore that is chemically attached to a nucleotide sequence. The fluorescent label may be attached to the 3' terminus of the nucleotide sequence, to a cleavable nucleobase of a non-reactive nucleotide sequence, or to a linker molecule that is attached to the nucleotide sequence.

As used herein, the term "gel material" is intended to mean a semi-rigid material that is permeable to liquids and gases. Typically, the gel material is a hydrogel that can swell when liquid is taken up and can contract when liquid is removed by drying.

As used herein, the term "grafted" is intended to mean covalently bound and not attached solely via non-covalent interactions, such as hybridization. In some instances, the quality control tracer, cleavable nucleotide sequence, non-reactive nucleotide sequence, and/or primer or primer nucleotide sequence are grafted to the gel material by formative of covalent bonds between functional groups on the tracer or sequence with functional groups in the gel material. As used herein, the term "co-graft" refers to grafting of more than one entity.

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. In the ring system, the heteroatom(s) may be present in either a non-aromatic or aromatic ring. The heterocyclyl group may have 3 to 20 ring members (i.e., the number of atoms making up the ring backbone, including carbon atoms and heteroatoms). The heterocyclyl group may be designated as "3-6 membered heterocyclyl" or similar designations. In some examples, the heteroatom(s) are O, N, or S.

The term "hydrazine" or "hydrazinyl" as used herein refers to a —NHNH$_2$ group.

As used herein, the term "hydrazone" or "hydrazonyl" as used herein refers to a group $R_a(R_b)C=N-NH_2$, in which $R_a$ and $R_b$ are previously defined herein.

As used herein, "hydroxyl" is an —OH group.

As used herein, the term "interstitial region" refers to an area in a substrate/support or on a surface that separates other areas of the substrate or surface. For example, an interstitial region can separate one feature of an array from another feature of the array. The two features that are separated from each other can be discrete, i.e., lacking contact with each other. In another example, an interstitial region can separate a first portion of a feature from a second portion of a feature. In many examples, the interstitial region is continuous whereas the features are discrete, for example, as is the case for a plurality of wells defined in an otherwise continuous surface. The separation provided by an interstitial region can be partial or full separation. Interstitial regions may have a surface material that differs from the surface material of the features defined in the surface. For example, features of an array can have an amount or concentration of gel material and a quality control tracer that exceeds the amount or concentration present at the interstitial regions. In some examples, gel material and quality control tracer(s) may not be present at the interstitial regions.

The term "linker molecule," as used herein, refers to a molecule that includes, at one end, a functional group that can attach to the detectable or fluorescent label and, at the other end, a functional group that can attach to a nucleotide sequence. The attachment points are covalent bonds. Similarly, the term "linked," as used herein, refers to two entities that are connected via one or more covalent bonds, either directly or via a linker molecule.

"Nitrile oxide," as used herein, means a "$R_aC\equiv N^+O^-$" group in which $R_a$ is selected from hydrogen, C1-6 alkyl, C2-6 alkenyl, C2-6 alkynyl, C3-7 carbocyclyl, C6-10 aryl, 5-10 membered heteroaryl, and 5-10 membered heterocyclyl. Examples of preparing nitrile oxide include in situ generation from aldoximes by treatment with chloramide-T or through action of base on imidoyl chlorides [RC(Cl)=NOH].

"Nitrone," as used herein, means a "$R_aR_bC=NR_c^+O^-$" group in which $R_a$ and $R_b$ are previously defined herein and $R_c$ is selected from C1-6 alkyl, C2-6 alkenyl, C2-6 alkynyl, C3-7 carbocyclyl, C6-10 aryl, 5-10 membered heteroaryl, and 5-10 membered heterocyclyl, as defined herein.

As used herein, a "nucleotide" includes a nitrogen containing heterocyclic base, a sugar, and one or more phosphate groups. Nucleotides are monomeric units of a nucleic acid sequence. In RNA, the sugar is a ribose, and in DNA a deoxyribose, i.e. a sugar lacking a hydroxyl group that is present at the 2' position in ribose. The nitrogen containing heterocyclic base (i.e., nucleobase) can be a purine base or a pyrimidine base. Purine bases include adenine (A) and guanine (G), and modified derivatives or analogs thereof. Pyrimidine bases include cytosine (C), thymine (T), and uracil (U), and modified derivatives or analogs thereof. The C-1 atom of deoxyribose is bonded to N-1 of a pyrimidine or N-9 of a purine.

The "non-reactive nucleotide sequence" referred to herein may be any nucleic acid sequence that does not actively participate in a particular DNA or RNA synthesis that is being performed. In some examples, the non-reactive nucleotide sequence may make up a portion of a quality control tracer. For example, the non-reactive nucleotide sequence may be a poly T sequence or a poly A sequence that is part of a cleavable nucleotide sequence that also includes an excision site. For another example, the non-reactive nucleotide sequence may be orthogonal to the primer nucleotide sequence(s) that is/are being used, and thus the non-reactive nucleotide sequence will not participate in the DNA or RNA synthesis which utilizes the primer nucleotide sequence(s).

As used herein, "predetermined ratio" refers to a ratio between two compounds in a mixture. The ratio is determined before the mixture is prepared. The ratio is the ratio of concentrations or molarities of the components in the mixture, or is the ratio of volumes of solutions of the two components that are blended to make the mixture. In some aspects, the "predetermined ratio" refers to the ratio of tracer and primer on the gel material, and in such cases, the ratio is based on the ratio of components reacted with the gel material and optionally takes into account any differential reactivity of the two components. In some aspects, the predetermined ratio for a mixture of the tracer and the primer is set at a percent volume of the primer (or primer mixture, where more than one primer sequence is used).

As used herein, the "primer nucleotide sequence" is defined as a single stranded nucleic acid sequence (e.g., single strand DNA or single strand RNA) that serves as a starting point for DNA or RNA synthesis. The 5' terminus of the sequencing primer may be modified to allow a coupling reaction with a gel material. The sequencing primer length can be any number of bases long and can include a variety of non-natural nucleotides. In an example, the sequencing primer is a short strand, including from 20 bases to 50 bases.

The term "untagged," as used herein, means that a nucleotide sequence does not have a fluorescent label attached thereto.

A "quality control tracer" includes a nucleotide sequence and a fluorescent label attached to the nucleotide sequence. The fluorescent label of the quality control tracer is capable of being detected in a quality control method. The fluorescent label of the quality control tracer is also capable of being removed, and the remaining portion of the tracer is either capable of participating in a sequencing method or is non-reactive during a sequencing method.

As used herein, a "site" refers to a location defined on or in a support where the gel material and a quality control tracer may be attached.

The terms "substrate" and "support" are used interchangeably herein, and refer to a surface in which or on which the site is located. The support is generally rigid and is insoluble in aqueous liquid. The support may be inert to a chemistry that is used to modify the gel material. For example, a support can be inert to chemistry used to attach the quality control tracer, to the gel material in a method set forth herein. Examples of suitable supports include glass and modified or functionalized glass, plastics (including acrylics, polystyrene and copolymers of styrene and other materials, polypropylene, polyethylene, polybutylene, polyurethanes, polytetrafluoroethylene (such as TEFLON® from Chemours), cyclic olefins/cyclo-olefin polymers (COP) (such as ZEONOR® from Zeon), polyimides, etc.), nylon, ceramics, silica or silica-based materials, siloxanes, silicon and modified silicon, carbon, metals, inorganic glasses, and optical fiber bundles.

A "thiol" functional group refers to —SH (e.g.,

).

As used herein, the terms "tetrazine" and "tetrazinyl" refer to six-membered heteroaryl group comprising four nitrogen atoms. Tetrazine can be optionally substituted.

"Tetrazole," as used herein, refer to five-membered heterocyclic group including four nitrogen atoms. Tetrazole can be optionally substituted.

As used herein, the term "well" refers to a discrete concave feature in a support having a surface opening that is completely surrounded by interstitial region(s) of the support surface. Wells can have any of a variety of shapes at their opening in a surface including, as examples, round, elliptical, square, polygonal, star shaped (with any number of vertices), etc. The cross-section of a well taken orthogonally with the surface can be curved, square, polygonal, hyperbolic, conical, angular, etc.

In some embodiments, the cleavable nucleotide sequence is cleavable via enzymatic cleavage or chemical cleavage.

In some instances, the cleavable nucleotide sequence comprises a linker molecule attaching the fluorescent label, wherein the linker molecule comprises a moiety cleavable via enzymatic cleavage or chemical cleavage. In some embodiments, the linker molecule comprises a vicinal diol and the chemical cleavage is accomplished by oxidative conditions, such as, for example, sodium periodate ($NaIO_4$). In other embodiments, the linker molecule is comprises a disulfide and the chemical cleavage is accomplished with a thiol or a tertiary phosphine; or the linker molecule is a silane and the chemical cleavage is accomplished with an acid or a fluoride ion; or the linker molecule is an azobenzene and the chemical cleavage is accomplished with a sodium dithionate ($Na_2S_2O_4$); or the linker molecule is a photocleavable group and the chemical cleavage is accomplished with light; or the linker molecule is an azido and the chemical cleavage is accomplished with a tertiary phosphine. In another example of the second aspect, the method further comprises cleaving the fluorescent label from the cleavable nucleobase of the non-reactive nucleotide sequence using an exonuclease.

In one example of this aspect, the quality control tracer comprises the cleavable nucleotide sequence, and the cleavable nucleotide sequence includes an excision site. In an example, the cleavable nucleotide sequence is a primer nucleotide sequence.

In another example of this aspect, the quality control tracer is the cleavable nucleotide sequence, and the cleavable nucleotide sequence includes a linker molecule attaching the fluorescent label. In some embodiments, the linker molecule comprises a functional group selected from the group consisting of a diol, a disulfide, a silane, an azobenzene, a photocleavable group, and an azido. In this other example of this aspect, the cleavable nucleotide sequence further includes a primer nucleotide sequence attached to the linker molecule.

In still another example of this aspect, the quality control tracer is the non-reactive nucleotide sequence, and the non-reactive nucleotide sequence further includes an excision site.

This aspect of the array can further comprise an untagged primer nucleotide sequence grafted to the gel material in each of the plurality of discrete wells, wherein the quality control tracer and the untagged primer nucleotide sequence are present in a predetermined ratio.

It is to be understood that any features of this aspect of the array may be combined together in any desirable manner and/or configuration.

In an example of the first aspect of the method, the quality control tracer is the cleavable nucleotide sequence, and the cleavable nucleotide sequence is the primer nucleotide sequence. In this example, the method can further comprise cleaving the fluorescent label from the primer nucleotide sequence after the density, or the distribution, or the density and distribution, of the primer nucleotide sequence is determined.

In another example of the first aspect of the method, the quality control tracer is the cleavable nucleotide sequence; the primer nucleotide sequence is untagged, prior to the detecting; the method further comprises grafting the primer nucleotide sequence to the gel material; the cleavable nucleotide sequence and the primer nucleotide sequence are present in a predetermined ratio; and the determining of the density, or the distribution, or the density and distribution, of the primer nucleotide sequence is based on the fluorescence and the predetermined ratio. This other example of the first aspect of the method can further comprise cleaving the fluorescent label from the cleavable nucleotide sequence. The cleaving is accomplished via enzymatic cleavage and/or chemical cleavage.

In still another example of the first aspect of the method, the quality control tracer is the non-reactive nucleotide sequence; the primer nucleotide sequence is untagged; prior to the detecting, the method further comprises grafting the primer nucleotide sequence to the gel material, wherein the non-reactive nucleotide sequence and the primer nucleotide sequence are present in a predetermined ratio; and the determining of the density, or the distribution, or the density and distribution, of the primer nucleotide sequence is based on the fluorescence and the predetermined ratio. This still other example of the first aspect of the method can further comprise cleaving the fluorescent label from the cleavable nucleobase of the non-reactive nucleotide sequence using an exonuclease.

It is to be understood that any features of the first aspect of the method may be combined together in any desirable manner. Moreover, it is to be understood that any combination of features of the first aspect of the method and/or of the array may be used together, and/or that any features from either or both of these aspects may be combined with any of the examples disclosed herein.

In one example of the second aspect, the method further comprises cleaving the fluorescent label from the cleavable nucleotide sequence via enzymatic cleavage or chemical cleavage. In some instances of this one example of the second aspect, the quality control tracer is the cleavable nucleotide sequence, the cleavable nucleotide sequence includes a linker molecule attaching the fluorescent label, and one of: the linker molecule comprises a diol and the chemical cleavage is accomplished with sodium periodate ($NaIO_4$); or the linker molecule comprises a disulfide and the chemical cleavage is accomplished with a thiol or a tertiary phosphine; or the linker molecule is a silane and the chemical cleavage is accomplished with an acid or a fluoride ion; or the linker molecule is an azobenzene and the chemical cleavage is accomplished with a sodium dithionate ($Na_2S_2O_4$); or the linker molecule is a photocleavable group and the chemical cleavage is accomplished with light; or the linker molecule is an azido and the chemical cleavage is accomplished with a tertiary phosphine.

In another example of the second aspect, the method further comprises cleaving the fluorescent label from the cleavable nucleobase of the non-reactive nucleotide sequence using an exonuclease.

It is to be understood that any features of this second aspect of the method may be combined together in any desirable manner. Moreover, it is to be understood that any combination of features of the first aspect and/or second aspect may be used together, and/or that any features from either or both of these aspects may be combined with any of the features of the array and/or any of the examples disclosed herein.

Examples of the arrays disclosed herein include several sites, each of which has an example of a quality control tracer attached to a gel material. The quality control tracer includes either a primer nucleotide sequence or is present in a predetermined ratio with the primer nucleotide sequence, and thus may be used in a quality control method to determine the density and/or distribution of the primer nucleotide sequence. The quality control tracer includes a fluorescent label that can be used in the quality control method and that can be cleaved from the tracer so that it does not interfere with sequencing. The inclusion of the quality control tracer in some instances alleviates the need to perform hybridization and dehybridization for quality control purposes. The examples disclosed herein enable the density and/or distribution of primer nucleotide sequences on a support to be assessed without having to load sequencing reagents and samples and without having to perform initial steps in a sequencing workflow.

The aspects and examples set forth herein and recited in the claims can be understood in view of the above definitions.

Figure 1:
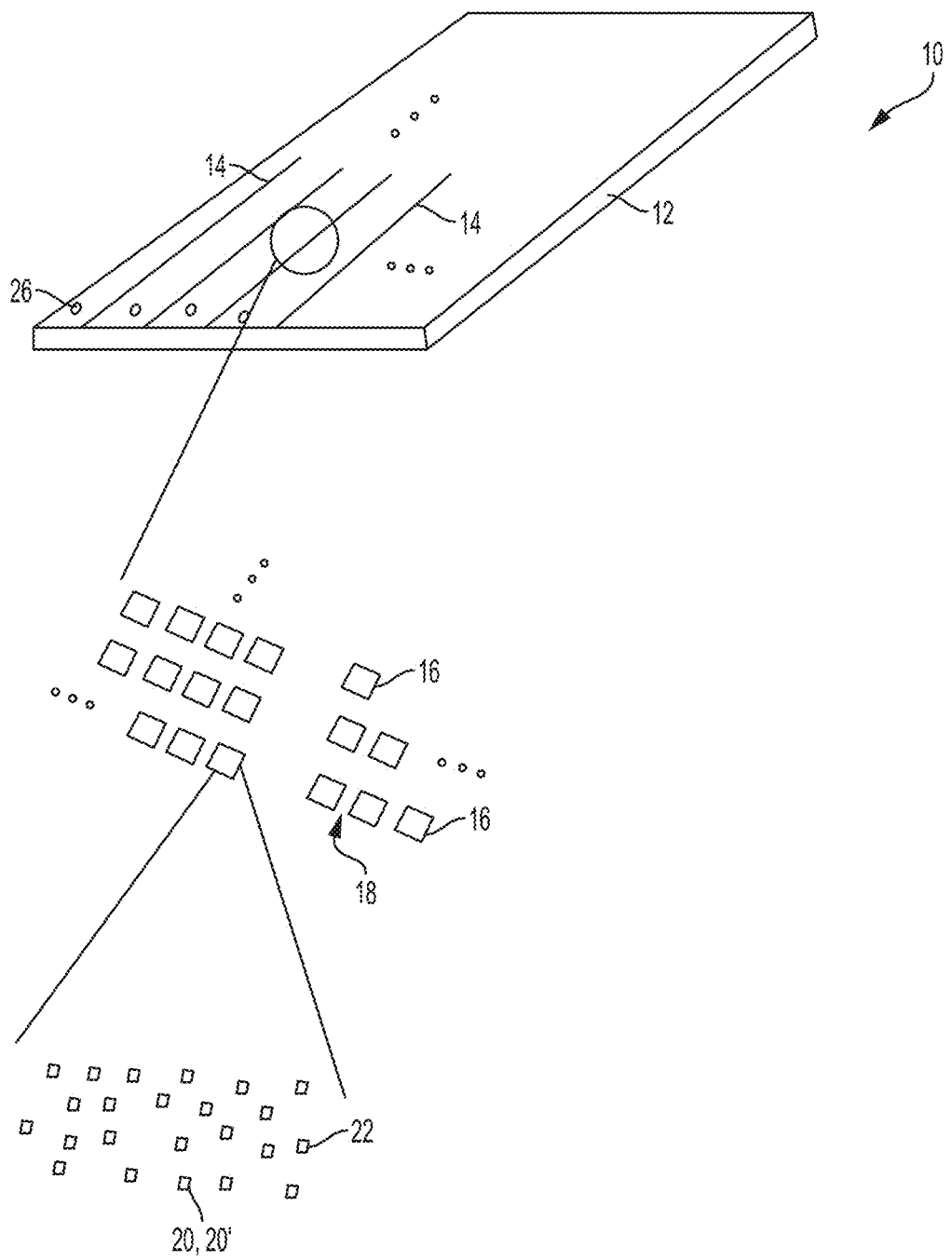
FIG. 1 is a diagrammatical representation of an example array according to the present disclosure, illustrating the overall layout of the array and detailing the arrangement of individual sites.

Referring now to FIG. 1, an example of the array 10 is depicted. In general, the array 10 includes a substrate or support 12 and lines or flow channels 14 across the support 12. Each of the flow channels 14 includes multiple sites 16, which are separated from one another by interstitial regions 18. At each site 16, at least quality control tracers 22 are attached to the gel material (24, 24', for example, in FIG. 2D). In some instances, in addition to the quality control tracers 22, separate primer nucleotide sequence(s) 20, 20' are also attached to the gel material 24.

The array 10 illustrated in FIG. 1 and discussed in the present disclosure may be disposed in or formed as a part of a flow cell, which is a chamber including a solid surface across which various carrier fluids, reagents, and so forth may be flowed. In an example, the flow cell may include the array 10 bonded to a top substrate through a sealing material (e.g., black polyimide or another suitable bonding material). The bonding takes place in bonding regions of the support 12, the sealing material, and the top substrate. The bonding regions may be located between the flow channels so that the sealing material physically separates one flow channel 14 from an adjacent flow channel 14 (to prevent cross-contamination) and may be located at the periphery of the flow cell (to seal the flow cell from external contamination). It is to be understood, however, that the bonding regions and the sealing material may be located in any desired region depending on the implementation. Bonding may be accomplished via laser bonding, diffusion bonding, anodic bonding, eutectic bonding, plasma activation bonding, glass frit bonding, or others methods known in the art.

Other examples of flow cells and related fluidic systems and detection platforms that can be integrated with the array 10 and/or readily used in the methods of the present disclosure are described, for example, in Bentley et al., Nature 456:53-59 (2008), WO 04/018497; U.S. Pat. No. 7,057,026; WO 91/06678; WO 07/123744; U.S. Pat. Nos. 7,329,492; 7,211,414; 7,315,019; and 7,405,281, and U.S. Patent Publication No. 2008/0108082, each of which is incorporated herein by reference in its entirety.

In some applications, the flow cell is used to perform controlled chemical or biochemical reactions in a reaction automation device, such as in a nucleotide sequencer. Ports 26 may be drilled through the support 12. By connecting to ports 26, the reaction automation device may control the flow of reagent(s) and product(s) in the sealed flow channels 14. The reaction automation device may, in some applications, adjust the pressure, temperature, gas composition and other environmental conditions of the flow cell. Further, in some applications, ports 26 may be drilled in the top substrate or in both the support 12 and the top substrate. In some applications, the reactions taking place in sealed flow channels 14 may be monitored through the top substrate and/or the support 12 by imaging or measurements of heat, light emission and/or fluorescence.

It is to be understood that the particular orientation of the flow channels 14, the sites 16, etc. may differ from those illustrated in FIG. 1. In some examples, the sites 16 are contiguous and thus need not be separated by interstitial regions 18.

The array 10 of FIG. 1, and examples of how the array 10 can be made, will now be described in more detail in reference to FIGS. 2A through 2D.

Figure 2A:
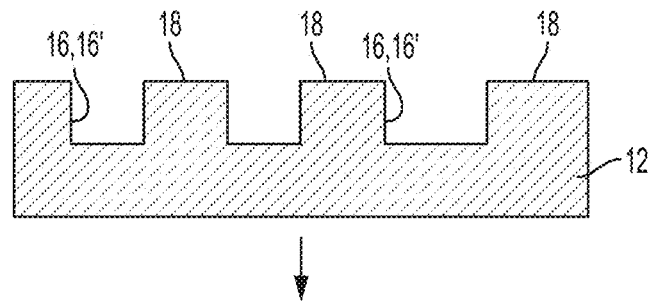
FIGS. 2A through 2D are cross-sectional views which together illustrate an example of a method for forming an array.

FIG. 2A depicts the support 12 having sites 16 defined therein and separated by interstitial regions 18. This support 12 has a patterned surface. A "patterned surface" refers to an arrangement of different regions (i.e., sites 16) in or on an exposed layer of the solid support 12. For example, one or more of the sites 16 can be features where one or more quality control tracers 22, and, in some instances, separate primer nucleotide sequence(s) 22 are present. The features can be separated by the interstitial regions 18, where quality control tracers 22 and separate primer nucleotide sequence(s) 20 are not present. Many different layouts of the sites 16 may be envisaged, including regular, repeating, and non-regular patterns. In an example, the sites 16 are disposed in a hexagonal grid for close packing and improved density. Other layouts may include, for example, rectilinear (i.e., rectangular) layouts, triangular layouts, and so forth. As examples, the layout or pattern can be an x-y format of sites 16 that are in rows and columns. In some other examples, the layout or pattern can be a repeating arrangement of sites 16 and/or interstitial regions 18. In still other examples, the layout or pattern can be a random arrangement of sites 16 and/or interstitial regions 18. The pattern may include spots, pads, wells, posts, stripes, swirls, lines, triangles, rectangles, circles, arcs, checks, plaids, diagonals, arrows, squares, and/or cross-hatches. Still other examples of patterned surfaces that can be used in the examples set forth herein are described in U.S. Pat. Nos. 8,778,849; 9,079,148; and 8,778,848, and U.S. Patent Publication No. 2014/0243224, each of which is incorporated herein by reference in its entirety.

The layout or pattern may be characterized with respect to the density of the sites 16 (i.e., number of sites 16) in a defined area. For example, the sites 16 may be present at a density of approximately 2 million per $mm^2$. The density may be tuned to different densities including, for example, a density of at least about 100 per $mm^2$, about 1,000 per $mm^2$, about 0.1 million per $mm^2$, about 1 million per $mm^2$, about 2 million per $mm^2$, about 5 million per $mm^2$, about 10 million per $mm^2$, about 50 million per $mm^2$, or more. Alternatively or additionally, the density may be tuned to be no more than about 50 million per $mm^2$, about 10 million per $mm^2$, about 5 million per $mm^2$, about 2 million per $mm^2$, about 1 million per $mm^2$, about 0.1 million per $mm^2$, about 1,000 per $mm^2$, about 100 per $mm^2$, or less. It is to be further understood that the density of sites 16 on the support 12 can be between one of the lower values and one of the upper values selected from the ranges above. As examples, a high density array may be characterized as having sites 16 separated by less than about 100 nm, a medium density array may be characterized as having sites 16 separated by about 400 nm to about 1 µm, and a low density array may be characterized as having sites 16 separated by greater than about 1 µm.

The layout or pattern may also or alternatively be characterized in terms of the average pitch, i.e., the spacing from the center of the site 16 to the center of an adjacent interstitial region 18 (center-to-center spacing). The pattern can be regular such that the coefficient of variation around the average pitch is small, or the pattern can be non-regular in which case the coefficient of variation can be relatively large. In either case, the average pitch can be, for example, at least about 10 nm, about 0.1 µm, about 0.5 µm, about 1 µm, about 5 µm, about 10 µm, about 100 µm, or more. Alternatively or additionally, the average pitch can be, for example, at most about 100 µm, about 10 µm, about 5 µm, about 1 µm, about 0.5 µm, about 0.1 µm, or less. The average pitch for a particular pattern of sites 16 can be between one of the lower values and one of the upper values selected from the ranges above. In an example, the sites 16 have a pitch (center-to-center spacing) of about 1.5 µm.

In some examples, the sites 16 are wells 16', and thus the support 12 includes an array of wells 16' in a surface thereof. The wells 16' (or other sites 16 with different configurations, such as shape, cross-section, etc.) may be fabricated using a variety of techniques, including, for example, photolithography, nanoimprint lithography, stamping techniques, embossing techniques, molding techniques, microetching techniques, printing techniques, etc. As will be appreciated by those in the art, the technique used will depend on the composition and shape of the support 12.

The wells 16' may be micro wells (having at least one dimension on the micron scale, e.g., about 1 µm to about 1000 µm) or nanowells (having at least one dimension on the nanoscale, e.g., about 1 nm to about 1000 nm). Each well 16' may be characterized by its volume, well opening area, depth, and/or diameter.

Each well 16' can have any volume that is capable of confining a liquid. The minimum or maximum volume can be selected, for example, to accommodate the throughput (e.g. multiplexity), resolution, analyte composition, or analyte reactivity expected for downstream uses of the array 10. For example, the volume can be at least about $1\times10^{-3}$ µm$^3$, about $1\times10^{-2}$µm$^3$, about 0.1 µm$^3$, about 1 µm$^3$, about 10 µm$^3$, about 100 µm$^3$, or more. Alternatively or additionally, the volume can be at most about $1\times10^4$µm$^3$, about $1\times10^3$ µm$^3$, about 100 µm$^3$, about 10 µm$^3$, about 1 µm$^3$, about 0.1 µm$^3$, or less. It is to be understood that the gel material 24 can fill all or part of the volume of a well 16'. The volume of the gel material 24 in an individual well 16' can be greater than, less than or between the values specified above.

The area occupied by each well opening on a surface can be selected based upon similar criteria as those set forth above for well volume. For example, the area for each well opening on a surface can be at least about $1\times10^{-3}$µm$^2$, about $1\times10^{-2}$ µm$^2$, about 0.1 µm$^2$, about 1 µm$^2$, about 10 µm$^2$, about 100 µm$^2$, or more. Alternatively or additionally, the area can be at most about $1\times10^3$µm$^2$, about 100 µm$^2$, about 10 µm$^2$, about 1 µm$^2$, about 0.1 µm$^2$, about $1\times10^{-2}$ µm$^2$, or less.

The depth of each well 16' can be at least about 0.1 µm, about 1 µm, about 10 µm, about 100 µm, or more. Alternatively or additionally, the depth can be at most about $1\times10^3$µm, about 100 µm, about 10 µm, about 1 µm, about 0.1 µm, or less.

In some instances, the diameter of each well 16' can be at least about 50 nm, about 0.1 µm, about 0.5 µm, about 1 µm, about 10 µm, about 100 µm, or more. Alternatively or additionally, the diameter can be at most about $1\times10^3$ µm, about 100 µm, about 10 µm, about 1 µm, about 0.5 µm, about 0.1 µm, about 50 nm, or less.

Figure 2B:
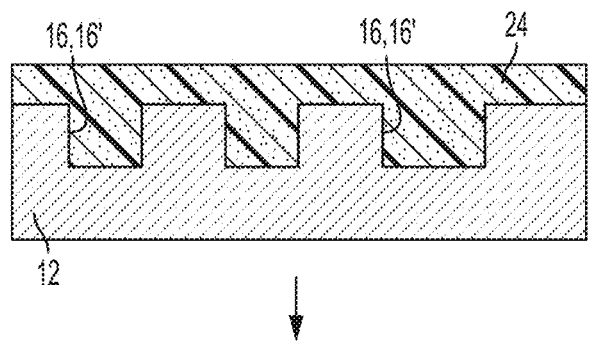
Figure 2C:
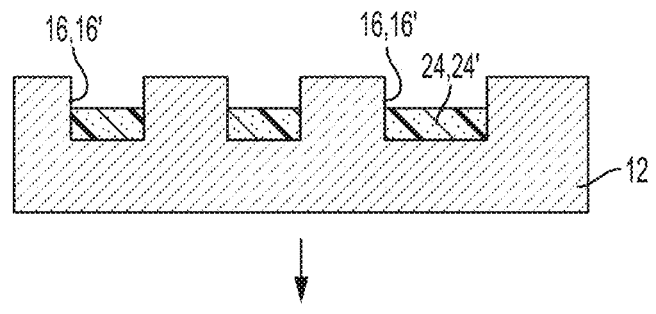
Figure 2D:
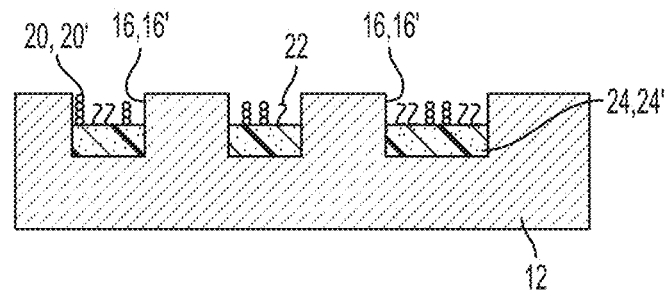

In the array 10 that is formed, the gel material 24 is positioned in each of the discrete wells 16'. Positioning the gel material 24 in each well 16' may be accomplished by first coating the patterned surface of the support 12 with the gel material 24, as shown in FIG. 2B, and then removing the gel material 24, for example via chemical or mechanical polishing, from at least the interstitial regions 18 on the surface of the structured support 12 between the wells 16'. These processes retain at least some of the gel material 24 in the wells 16' but remove or inactivate at least substantially all of the gel material 24 from the interstitial regions 18 on the surface of the structured support 12 between the wells 16'. As such, these processes create gel pads 24' (FIG. 2D) used for sequencing that can be stable over sequencing runs with a large number of cycles.

Particularly useful gel materials 24 will conform to the shape of the site 16 where it resides. Some useful gel materials 24 can both (a) conform to the shape of the site 16 (e.g., well 16' or other concave feature) where it resides and (b) have a volume that does not at least substantially exceed the volume of the site 16 where it resides.

One example of a suitable gel material 24 includes a polymer represented by Formula (I):

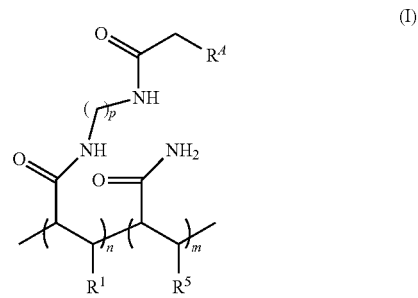

wherein:

$R^1$ is H or optionally substituted alkyl;

$R^A$ is selected from the group consisting of azido, optionally substituted amino, optionally substituted alkenyl, optionally substituted hydrazone, optionally substituted hydrazine, carboxyl, hydroxy, optionally substituted tetrazole, optionally substituted tetrazine, nitrile oxide, nitrone, and thiol; $R^5$ is selected from the group consisting of H and optionally substituted alkyl;

each of the —(CH$_2$)$_p$— can be optionally substituted;

p is an integer in the range of 1 to 50;

n is an integer in the range of 1 to 50,000; and m is an integer in the range of 1 to 100,000.

In the structure of Formula (I), one of ordinary skill in the art will understand that the "n" and "m" subunits are recurring subunits that are present in a random order throughout the polymer. One of ordinary skill will also recognize that other monomeric components may be present in the polymer.

A particular example of a gel material 24 is poly(N-(5-azidoacetamidylpentyl)acrylamide-co-acrylamide ("PAZAM") (described, for example, U.S. Patent Publication Nos. 2014/0079923 A1 and 2015/0005447 A1, each of which is incorporated herein by reference in its entirety), which comprises the structure shown below:

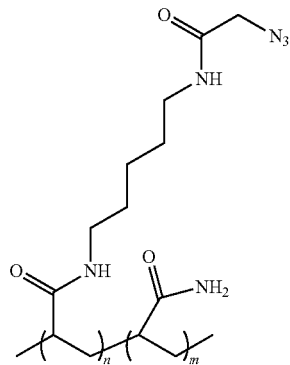

wherein n is an integer in the range of 1-20,000, and m is an integer in the range of 1-100,000. As with Formula (I), one of ordinary skill in the art will recognize that the "n" and "m" subunits are recurring units that are present in random order throughout the polymer structure.

The molecular weight of the PAZAM may range from about 10 kDa to about 1500 kDa, or may be, in a specific example, about 312 kDa.

In some examples, PAZAM is a linear polymer. In some other embodiments, PAZAM is a lightly cross-linked polymer. In other examples, PAZAM comprises branching.

Other examples of suitable gel materials 24 include those having a colloidal structure, such as agarose; or a polymer mesh structure, such as gelatin; or a cross-linked polymer structure, such as polyacrylamide polymers and copolymers, silane free acrylamide (SFA, see, for example, U.S. Patent Publication No. 2011/0059865, which is incorporated herein by reference in its entirety), or an azidolyzed version of SFA. Examples of suitable polyacrylamide polymers may be formed from acrylamide and an acrylic acid or an acrylic add containing a vinyl group as described, for example, in WO 2000/031148 (incorporated herein by reference in its entirety) or from monomers that form [2+2] photo-cycloaddition reactions, for example, as described in WO 2001/001143 or WO 2003/014392 (each of which is incorporated herein by reference in its entirety).

The gel material 24 may be a preformed gel material. Preformed gel materials may be coated using spin coating, or dipping, or flow of the gel under positive or negative pressure, or techniques set forth in U.S. Pat. No. 9,012,022, which is incorporated herein by reference in its entirety. Dipping or dip coating may be a selective deposition technique, depending upon the support 12 and the gel material 24 that are used. As an example, the patterned support 12 is dipped into a preformed gel material 24, and the gel material 24 may fill the sites 16 selectively (i.e., the gel material 24 does not deposit on the interstitial regions 18), and polishing (or another removal process) may not be necessary.

Preformed PAZAM may be coated on the patterned support 12 using spin coating, or dipping, or flow of the gel under positive or negative pressure, or techniques set forth in U.S. Pat. No. 9,012,022. The attachment of PAZAM may also take place by chemical reaction to form a covalent bond, or via a surface initiated atom transfer radical polymerization (SI-ATRP) to a silanized surface.

In some examples, the support surface is treated with an alkene-derivatized silane, wherein the alkene portion may be linear, branched, or cyclic. In some examples, the silane reagent is $(RO)_3$Si-Linker-Alkene, and in other examples, the silane reagent is $(RO)_3$Si—$C_{2-6}$alkylene-cycloalkene, and in other examples, the silane reagent is $(RO)_3$Si-$CH_2CH_2$-norbornene, where each R is a $C_{1-4}$alkyl or is methyl or ethyl. The gel material 24, such as PAZAM, is covalently bound to the alkene-derivatized silanes under thermal or uv conditions.

In other examples, the support 12 surface may be pretreated with an amino-derivatized silane, such as an amino-propyl-trialkoxysilane (APTS), for example 3-aminopropyl-trimethoxysilane (APTMS) or 3-aminopropyl-triethoxysilane (APTES) to covalently link silicon to one or more oxygen atoms on the surface (without intending to be held by mechanism, each silicon may bond to one, two or three oxygen atoms). This chemically treated surface is baked to form an amine group monolayer. The amine groups are then reacted with Sulfo-HSAB to form an azido derivative. UV activation at 21° C. with 1 $J/cm^2$ to 30 $J/cm^2$ of energy generates an active nitrene species, which can readily undergo a variety of insertion reactions with the PAZAM.

Other examples for coating PAZAM on the support 12 are described in U.S. Patent Publication No. 2014/0200158, which is incorporated herein by reference in its entirety), and include ultraviolet (UV) mediated linking of PAZAM monomers to an amine-functionalized surface, or a thermal linkage reaction involving an active group (acryloyl chloride or other alkene or alkyne-containing molecule) with subsequent deposition of PAZAM and application of heat.

The gel material 24 may be formed by applying a liquid that subsequently forms the gel material 24. An example of applying liquid that subsequently forms the gel material 24 is the coating of an array of sites 16 with silane-free acrylamide and N-[5-(2-bromoacetyl) aminopentyl]acrylamide (BRAPA) in liquid form and allowing the reagents to form a gel by polymerization on the surface. Coating of an array in this way can use chemical reagents and procedures as set forth in U.S. Patent Publication No. 2011/0059865.

The gel material 24 may be covalently linked to the support 12 (at the sites 16) or may not be covalently linked to the support 12. The covalent linking of the polymer to the sites 16 is helpful for maintaining the gel in the structured sites 16 throughout the lifetime of the array 10 during a variety of uses. However, as noted above and in many examples, the gel material 24 need not be covalently linked to the sites 16. For example, silane free acrylamide, SFA, is not covalently attached to any part of the support 12.

As mentioned above, FIG. 2C illustrates the removal of the gel material 24 from the interstitial regions 18. Removal may be accomplished via polishing. Polishing may be a mechanical and/or chemical treatment process.

Mechanical polishing can be carried out by applying abrasive forces to the surface of the solid support 12 (having the gel material 24 thereon). Example methods include abrasion with a slurry of beads, wiping with a sheet or cloth, scraping, or the like. It will be understood that beads used for polishing may or may not be spherical, and can have irregular shapes, polygonal shapes, ovoid shapes, elongated shapes, cylindrical shapes, etc. The surface of the beads can be smooth or rough. Any of a variety of particles can be useful as beads for polishing. One example of polishing includes using a lintless (cleanroom grade) wipe coated with a 3 μm silica bead slurry (10% w/v in water) to remove the gel material 24 from the interstitial regions 18. A polishing wheel/grinder can also be used with this slurry. Mechanical polishing can also be achieved using a fluid jet or gas (e.g., air or inert gas such as Argon or Nitrogen) jet to remove gel from interstitial regions 18.

Chemical polishing techniques, such as hydrolysis or radical-based degradation of acrylamide (e.g. via exposure to benzoyl peroxide or dilute hydrogen peroxide) may be used. During this form of polishing, the chemicals can be provided in a solid, liquid, gas or plasma state. Accordingly, plasma polishing can be useful in some examples.

Polishing can also involve a combination of chemical and mechanical polishing methods, where a chemical slurry containing a colloidal suspension of particles is used to mechanically exfoliate and then chemically dissolve displaced portions of gel material 24 from interstitial regions 18.

Other methods to polish or clean the interstitial regions 18 include adhesive based techniques, for example, techniques wherein a rigid, planar adhesive film with affinity to the gel material 24 is applied, thereby making intimate contact (e.g., via chemical linkage) with the gel material 24 in interstitial regions 18. The mechanical removal/peeling of this adhesive film will result in the mechanical removal of the gel material 24 from interstitial regions 18, while leaving gel material 24 in the sites 16.

In one example, thiophosphate-grafted SFA can be removed from interstitial regions 18 on a support 12 surface as follows: a water-dampened Whatman wipe can be dabbed into aluminum oxide (~100 mg, 0.3 um) or steel beads, and then the formed slurry can be rubbed on the surface of the support (having the thiophosphate-grafted SFA thereon), in small concentric circles, using even pressure, and then a clean water-wet Whatman wipe can be used to remove the slurry and the thiophosphate-grafted SFA from the surface.

The mechanical and chemical polishing methods exemplified herein for removing gel material 24 from interstitial regions 18 can also be used to inactivate gel material at interstitial regions 18, whether or not the gel material 24 is removed. For example, the gel material 24 can be inactivated with respect to the ability to attach the quality control tracers 22 and separate primer nucleotide sequence(s) 20, 20'.

After the gel material 24 is positioned in each well 16', the quality control tracers 22, and, in some instances separate primer nucleotide sequence(s) 20, 20' are grafted to the gel material 24. The attachment technique that is used, and whether separate, primer nucleotide sequences 20, 20' are included will depend, in part, upon the quality control tracer 22 that is utilized. Various examples of the quality control tracer 22 are shown in FIGS. 3A through 3D and in FIG. 4. Each example will now be described.

Figure 3A:
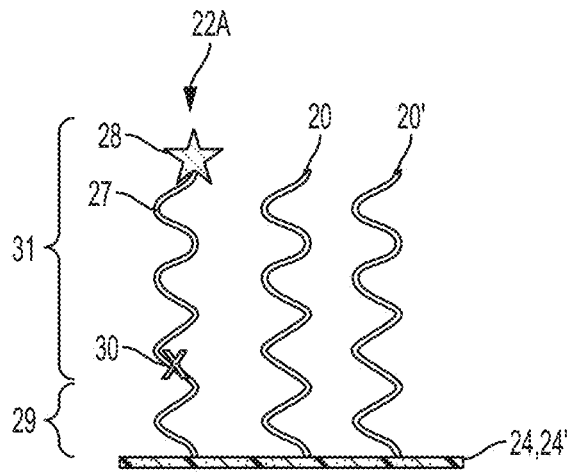
FIGS. 3A through 3D are schematic illustrations of different examples of quality control tracers disclosed herein.

FIG. 3A depicts an example of the quality control tracer 22A that is included on the gel material 24/gel pad 24' with separate primer nucleotide sequence(s) 20, 20'. In this example, the quality control tracer 22A is a cleavable nucleotide sequence 27 tagged, at its 3' end, with a fluorescent label 28, and the primer nucleotide sequence(s) 20, 20 are untagged primer nucleotide sequence(s).

The cleavable nucleotide sequence 27 of FIG. 3A may include a functional group at its 5' end that is capable of attaching to the gel material 24. Examples of this functional group include an alkyne, a norbornyl (or other cycloalkenyls), a copper free click moiety (e.g., dibenzocyclooctyne (DIBO), other cycloalkynes, or others), and a thiol. This functional group may be selected based upon the gel material 24 that is used. For example, alkynes, norbornyls, and copper free click moieties may react with azides of PAZAM via click reactions, and thiols may react with SFA. In some embodiments, the functional group is an alkyne.

The cleavable nucleotide sequence 27 of FIG. 3A may also include a functional group at its 3' end that is capable of attaching to the fluorescent label 28. An example of this functional group, which can be used during oligonucleotide synthesis, is 5'-Dimethoxytrityl-5-[N-(trifluoroacetylaminohexyl)-3-acrylimido]-2'-deoxyUridine,3'-[(2-cyanoethyl)-(N,N-diisopropyl)]-phosphoramidite (i.e., amino modifier C6 dT). Other examples include 5'-Dimethoxytrityl-N-dimethylformamidine-5-[N-(trifluoroacetylaminohexyl)-3-acrylimido]-2'-deoxyCytidine, 3'-[(2-cyanoethyl)-(N,N-diisopropyl)]-phosphoramidite (amino modifier C6 dC) and the use of solid supports such as (2-Dimethoxytrityloxymethyl-6-fluorenylmethoxycarbonylamino-hexane-1-succinoyl)-long chain alkylamino-CPG. The functional group at the 3' end may be selected based upon the fluorescent label 28 that is used.

The detectable or fluorescent label 28 may be any suitable fluorophore that can attach to the cleavable nucleotide sequence 27, e.g., at the 3' end (or at or near the 3' end). Examples of suitable fluorescent labels 28 include TEXAS RED® (a sulfonyl chloride dye, ThermoFisher Scientific), CY7®, CY7.5® or sulfo-Cyanine7 NHS ester (cyanine dyes from Lumiprobe), a red wavelength dye, such as TEX™ 615 (Exiqon), fluorescent dyes, such as those in the ALEXA FLUOR® series (ThermoFisher Scientific), Atto dyes (e.g., Atto 488, the structure of which is

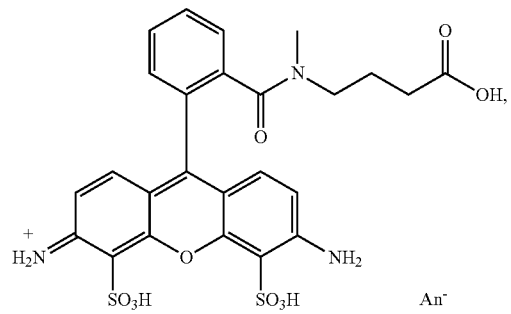 [SMILES: CN(CCCC(=O)O)C(=O)c1ccccc1-c1c2ccc(=N)c(S(=O)(=O)O)c-2oc2c(S(=O)(=O)O)c(N)ccc12]

the Atto-Tec series, from Atto-Tec), FAM™ dyes (derivatives of fluorescein, Integrated DNA Technologies), xanthene fluorophores, such as CAL FLUOR® dyes (e.g., CAL FLUOR® Gold 540, CAL FLUOR® Orange 460, CAL FLUOR® Red 590, CAL FLUOR® Red 610, and CAL FLUOR® Red 635, from LGC Biosearch Technologies), indocarbocyanine dyes, such as QUASAR® dyes (e.g., QUASAR® 570, QUASAR® 670, and QUASAR® 705, from LGC Biosearch Technologies), or any other suitable fluorophore known to those of ordinary skill in the art. Other examples include DYLIGHT™ 488 (an amine reactive dye), or a fluorophore with an emission maximum of approximately 518 nm. In some aspects, the fluorescent label is a xanthene fluorophore. In some aspects, the xanthene fluorophore has an emission maximum in the range of 540 to 640 nm, or 540 to 570 nm, or 580 to 640 nm. In other aspects, the xanthene fluorophore has an emission maximum in the range of 585 to 640 nm. In other aspects, the xanthene fluorophore emits in the red region of the spectrum. In other aspects, the xanthene fluorophore has an emission maximum of approximately 591 nm, or 610 nm, or 637 nm. Other suitable detectable labels include non-fluorescent labels, such as plasmonic nanoparticles (detected by, e.g., SPR sensing) or quantum dots. In some aspects, the detectable label is derivatized with an amino-reactive group such as an NHS to allow for coupling to an oligonucleotide sequence.

The fluorescent label 28 may be attached to the cleavable nucleotide sequence 27 using any suitable method, such as template directed ligation, polymerase-mediated oligonucleotide elongation, chemical synthesis, etc. The attachment of the fluorescent label 28 may take place during nucleotide synthesis (e.g., using mutant DNA polymerases which allow for synthesis of a complementary, fluorophore-labeled DNA or using fluorescent label-modified monomers during solid phase oligonucleotide synthesis) or after nucleotide synthesis (e.g., via coupling chemistry to conjugate the label 28 onto a previously installed functional group located at the 3' position).

This example of the cleavable nucleotide sequence 27 includes a cleavable portion 31 and a remaining portion 29. The cleavable portion 31 includes the fluorescent label 28 (and any functional group used to attached the fluorescent label 28), any sequence of nucleotides, and an excision site 30. As such, the cleavable portion 31 of the cleavable nucleotide sequence 27 can be removed when the sequence 27 is exposed to an enzyme that targets the nucleotide located at the excision site 30. The portion 29 of the cleavable nucleotide sequence 27 that remains attached to the gel material 24 after enzymatic cleavage is a non-reactive nucleotide sequence, and thus will not participate in or interfere with a sequencing operation that is to be performed or is being performed. The remaining portion may be a short poly T or poly A sequence, or may be a sequence that is orthogonal to the primer nucleotide sequence(s) 20, 20' also attached to the gel material 24.

The quality control tracer 22A in FIG. 3A is used (e.g., in examples of the quality control method disclosed herein) in combination with separate primer nucleotide sequence(s) 20, 20'. Examples of suitable primer nucleotide sequence(s) 20, 20' include forward amplification primers or reverse amplification primers for hybridization to a complementary sequence and amplification of a sequence. Some specific examples of suitable primer nucleotide sequence(s) 20, 20' include P5 and/or P7 primers. The P5 and P7 primers are used on the surface of commercial flow cells sold by Illumina, Inc., for sequencing on HISEQ®, HISEQX®, MISEQ®, NEXTSEQ®, GENOME ANALYZER®, and other instrument platforms. The P5 and P7 primers, as well as other sequencing primers 20, 20', may be modified at the 5' end with a group that is capable of reacting with a functional group of the gel material 24. One example of a suitable functional group is bicyclo[6.1.0] non-4-yne (BCN), which can react with an azide of the gel material 24. Other examples of terminated primers include a tetrazine terminated primer, a norbornene terminated primer, an alkyne terminated primer, an amino terminated primer, an epoxy or glycidyl terminated primer, a thiophosphate terminated primer, and a triazolinedione terminated primer. Examples of the P5 and P7 primers, which may be alkyne terminated, include the following:

```
P5:
                                      (SEQ. ID NO. 1)
5'-alkyne-AATGATACGGCGACCACCGAGAUCTACAC-3'

P7:
                                      (SEQ. ID NO. 2)
5'-alkyne-CAAGCAGAAGACGGCATACGAG*AT-3'
``` and derivatives thereof. In some examples, the P7 sequence includes a modified guanine at the G* position, e.g., an 8-oxo-guanine. In other examples, the * indicates that the bond between the G* and the adjacent 3' A is a phosphorothioate bond. In some examples, the P5 and/or P7 primers include unnatural linkers.

Optionally, one or both of the P5 and P7 primers can include a poly T tail. The poly T tail is generally located at the 5' end of the sequence (e.g., between the 5' terminal base and the alkyne unit), but in some cases can be located at the 3' end. The poly T sequence can include any number of T nucleotides, for example, from 2 to 20.

While the P5 and P7 primers are given as examples, it is to be understood that any suitable amplification primers can be used in the examples presented herein. One of skill in the art will understand how to design and use primer nucleotide sequence(s) 20, 20' that are suitable for capture and amplification of nucleic acids as presented herein.

An example of a quality control tracer 22A is orthogonal to the P5 and P7 primer nucleotide sequence(s) 20, 20'. In some aspects, the quality control tracer includes a uracil excision site.

In some aspects, the quality control tracer includes one of the following sequences:

```
                                      (SEQ. ID NO. 3)
(1) 5' CATCTAGGCATCTAAGCATCAAUCTTACA 3'

(SEQ. ID NO. 4)
(2) 5' ACATACATACATACATACAUACATACA 3'
```

```
                                      (SEQ. ID NO. 5)
(3) 5' ATTGATTGATTGATTGATUGATTGAT 3'
``` where U is cleavage site. In some aspects, U is a uracil excision site.

In some aspects, the quality control tracer comprises a polyT sequence at the 5' end of the sequence. In some aspects, the polyT region comprises 2 to 20, or 3, 4, 5, 6, or 7 T nucleotides. In some aspects, the polyT region comprises 4, 5, or 6 T bases. In other aspects, the polyT region comprises 6 T nucleotides. In some aspects, the sequence is:

```
                                      (SEQ. ID NO. 6)
(1) 5' polyT-CATCTAGGCATCTAAGCATCAAUCTTACA 3'
or (SEQ. ID NO. 7)
(2) 5' polyT-ACATACATACATACATACAUACATACA 3'
or (SEQ. ID NO. 8)
(3) 5' polyT-ATTGATTGATTGATTGATUGATTGAT 3'.
```

In some aspects, the quality control tracer includes TEXAS RED® as the fluorescent label. In some aspects, the quality control tracer is:

```
                                      (SEQ. ID NO. 9)
5'-alkyne-CATCTAGGCATCTAAGCATCAAUCTTACA

[Amino C6 dT-Texas Red]-3'
or (SEQ. ID NO. 10)
5'-alkyne-ACATACATACATACATACAUACATACA

[Amino C6 dT-Texas Red]-3'
or (SEQ. ID NO. 11)
5'-alkyne-ATTGATTGATTGATTGATUGATTGAT

[Amino C6 dT-Texas Red]-3'.
```

In some aspects, these tracers also include a polyT region between between the alkyne and the rest of the sequence, as described herein.

In some aspects, the quality control tracer is:

```
                                      (SEQ. ID NO. 12)
5'-alkyne-CATCTAGGCATCTAAGCATCAAUCTTACA

[Amino C6 dT-xanthene fluorophore]-3'
or (SEQ. ID NO. 13)
5'-alkyne-ACATACATACATACATACAUACATACA

[Amino C6 dT-xanthene fluorophore]-3'
or (SEQ. ID NO. 14)
5'-alkyne-ATTGATTGATTGATTGATUGATTGAT

[Amino C6 dT-xanthene fluorophore]-3'.
```

In some aspects, these tracers also include a polyT region at the 5' end between the alkyne and the rest of the sequence, as described herein.

In some aspects, the quality control tracer comprises an alkyne terminus, and in some aspects, that is a 5'-hexyne terminus. Suitable termini are used to attach the tracer to the gel material.

In some aspects, the quality control tracer is:

```
                                              (SEQ. ID NO. 15)
5'-alkyne-TTTTTTACATACATACATACATACAUACATACA

[Amino C6 dT-xanthene fluorophore]-3'.
```

In some aspects, the alkyne is a hexyne. In some aspects, the U cleavage site is a uracil excision site. In some aspects, the xanthene fluorophore has an emission maximum in the range of 585 to 640 nm. In other aspects, the xanthene fluorophore emits in the red region of the spectrum. In other aspects, the xanthene fluorophore has an emission maximum of approximately 591 nm, or 610 nm, or 637 nm. In some aspects, the fluorophore is TEXAS RED®.

In some aspects, where the quality control tracer comprises both a primer sequence and the detectable label, the quality control tracer includes one of the following sequences:

```
                                              (SEQ. ID NO. 16)
5'-AATGATACGGCGACCACCGAGAUCTACA-3'

(SEQ. ID NO. 17)
5'-AATGATACGGCGACCACCGAGAUCACAC-3'

(SEQ. ID NO. 1)
5'-AATGATACGGCGACCACCGAGAUCTACAC-3'.
```

In some aspects, the quality control tracer includes a polyT region as described above. In some examples, the quality control tracer comprises one of the following sequences:

```
                                              (SEQ. ID NO. 18)
5'-(polyT or TTTTTT)AATGATACGGCGACCACCGAGAUC

TACA-3'

(SEQ. ID NO. 19)
5'-(polyT or TTTTTT)AATGATACGGCGACCACCGAGAUC

ACAC-3'

(SEQ. ID NO. 20)
5'-(polyT or TTTTTT)AATGATACGGCGACCACCGAGAUC

TACAC-3'.
```

In some aspects, the quality control tracer includes a terminus that allows for grafting to the gel material. In some examples, the terminus is an alkyne or a hexyne moiety. Thus, in some aspects, the quality control tracer comprises one of the following sequences:

```
                                              (SEQ. ID NO. 18)
5'-(alkyne)-(polyT or TTTTTT)AATGATACGGCGACC

ACCGAGAUCTACA-3'

(SEQ. ID NO. 19)
5'-(alkyne)-(polyT or TTTTTT)AATGATACGGCGACC

ACCGAGAUCACAC-3'
```

-continued
```
                                              (SEQ. ID NO. 20)
5'-(alkyne)-(polyT or TTTTTT)AATGATACGGCGACC

ACCGAGAUCTACAC-3'.
```

In some aspects, the quality control tracer comprises a xanthene fluorophore as described herein, or Texas Red. In some aspects, the quality control tracer comprises one of the following sequences:

```
                                              (SEQ. ID NO. 21)
5'-(alkyne)-(polyT or TTTTTT)AATGATACGGCGACC ACCGAGAUCTACA(amino C6 dT-xanthene fluorophore)-3'

(SEQ. ID NO. 22)
5'-(alkyne)-(polyT or TTTTTT)AATGATACGGCGACC

ACCGAGAUC(amino C6 dT-xanthene fluorophore)ACAC-3'

(SEQ. ID NO. 23)
5'-(alkyne)-(polyT or TTTTTT)AATGATACGGCGACC

ACCGAGAUCTACAC(amino C6 dT xanthene fluorophore)-3'.
```

When the quality control tracer 22A in FIG. 3A is used, it is to be understood that it is present in a predetermined ratio with respect to the separate primer nucleotide sequence(s) 20, 20'. The predetermined ratio can be used in an example of the quality control method disclosed herein to indirectly determine the density and/or distribution of the separate primer nucleotide sequence(s) 20, 20'.

To form the example shown in FIG. 3A, sequential grafting or co-grafting may be used.

Sequential grafting may be accomplished by exposing the support 12 (having the gel material 24 in the sites 16) to a solution or mixture containing the quality control tracer 22A and incubating, and then to a solution or mixture containing the primer nucleotide sequence(s) 20, 20' and incubating. Alternatively, sequential grafting may be accomplished by exposing the support 12 (having the gel material 24 in the sites 16) to a solution or mixture containing the primer nucleotide sequence(s) 20, 20' and incubating, and then to a solution or mixture containing the quality control tracer 22A and incubating.

Co-grafting may be accomplished by exposing the support 12 (having the gel material 24 in the sites 16) to a solution or mixture containing the quality control tracer 22A and the primer nucleotide sequence(s) 20, 20', and then incubating. Exposure of the support 12 to this solution or mixture may be accomplished by depositing a mixture of the quality control tracer 22A and the primer nucleotide sequence(s) 20, 20' onto the support 12. In an example, the solution or mixture may be drawn across the gel material 24 coated support 12 (shown in FIG. 2C).

In any of the grafting examples used to form the example shown in FIG. 3A, incubation takes place at a predetermined temperature which depends, in part, upon the quality control tracer 22A and the primer nucleotide sequence(s) 20, 20' used. As examples, incubation may be accomplished at a temperature ranging from about 50° to about 70° C.

Also in any of the grafting examples used to form the example shown in FIG. 3A, the solution may include the quality control tracer 22A and/or the primer nucleotide sequence(s) 20, 20', water, a buffer, and a catalyst. The quality control tracer 22A and/or the primer nucleotide sequence(s) 20, 20', whether present in the same solution/mixture or separate solutions/mixtures, may be present at any desired predetermined ratio.

Figure 3B:
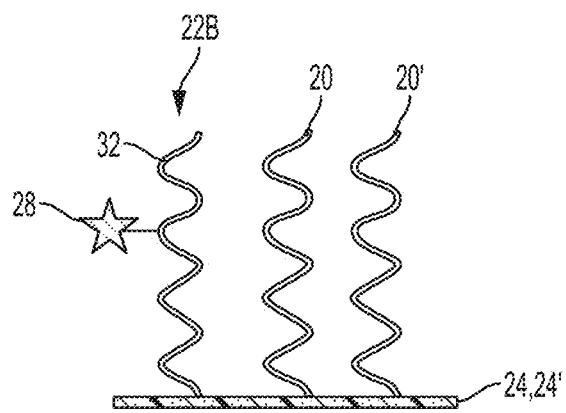

FIG. 3B depicts another example of the quality control tracer 22B that is included on the gel material 24/gel pad 24' with separate primer nucleotide sequence(s) 20, 20'. In this example, the quality control tracer 22B is a non-reactive nucleotide sequence 32 with the fluorescent label 28 attached to a cleavable nucleobase, and the primer nucleotide sequence(s) 20, 20 are untagged primer nucleotide sequence(s).

The non-reactive nucleotide sequence 32 of this example of the quality control tracer 22B remains at least substantially intact after the quality control method is performed and while sequencing is performed, and thus the sequence 32 is orthogonal to the primer nucleotide sequence(s) 20, 20' also attached to the gel material 24.

The non-reactive nucleotide sequence 32 of FIG. 3B may include a functional group at its 5' end that is capable of attaching to the gel material 24. Examples of this functional group include an alkyne, a norbornyl (or other cycloalkenyls), a copper free click moiety (e.g., dibenzocyclooctyne (DIBO), other cycloalkynes, or others), and a thiol. This functional group may be selected based upon the gel material 24 that is used. For example, alkynes, norbornyls, and copper free click moieties may react with azides of PAZAM via click reactions, and thiols may react with SFA.

In this example of the quality control tracer 22B, the fluorescent label 28 is attached to a cleavable nucleobase of the sequence 32. The nucleobase to which the fluorescent label 28 is attached is one that can be cleaved by an exonuclease, which catalyzes the excision of the particular base, while leaving the phosphodiester backbone intact.

In this example, the fluorescent label 28 may be attached near (e.g., within 10 bases of) but not directly at, the 3' end of the sequence 32. Any of the previously described fluorescent labels 28 may be used, as long as the selected label can covalently attach to a desirable nucleobase of the non-reactive nucleotide sequence 32.

The quality control tracer 22B in FIG. 3B is used (e.g., in examples of the quality control method disclosed herein) in combination with separate primer nucleotide sequence(s) 20, 20'. Examples of suitable primer nucleotide sequence(s) 20, 20' include forward amplification primers or reverse amplification primers for hybridization to a complementary sequence and amplification of a sequence. Some specific examples of suitable primer nucleotide sequence(s) 20, 20' include the previously described P5 or P7 primers.

When the quality control tracer 22B in FIG. 3B is used, it is to be understood that it is present in a predetermined ratio with respect to the primer nucleotide sequence(s) 20, 20'. The predetermined ratio can be used in an example of the quality control method disclosed herein to indirectly determine the density and/or distribution of the primer nucleotide sequence(s) 20, 20'.

To form the example shown in FIG. 3B, sequential grafting or co-grafting may be used as previously described, except that the quality control tracer 22B is used instead of the quality control tracer 22A. In any of the grafting examples used to form the example shown in FIG. 3B, incubation takes place at a predetermined temperature which depends, in part, upon the quality control tracer 22B and the primer nucleotide sequence(s) 20, 20' used. Also in any of the grafting examples used to form the example shown in FIG. 3B, the solution may include the quality control tracer 22B and/or the primer nucleotide sequence(s) 20, 20', water, a buffer, and a catalyst. The quality control tracer 22B and/or the primer nucleotide sequence(s) 20, 20', whether present in the same solution/mixture or separate solutions/mixtures, may be present at any desired predetermined ratio.

Figure 3C:
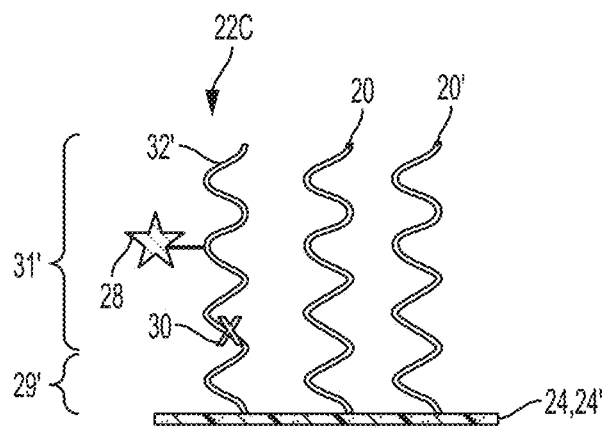

FIG. 3C depicts still another example of the quality control tracer 22C that is included on the gel material 24/gel pad 24' with separate primer nucleotide sequence(s) 20, 20'. In this example, the quality control tracer 22C is a non-reactive nucleotide sequence 32' with the fluorescent label 28 attached to a cleavable nucleobase (near the 3' end) and with an excision site 30, and the primer nucleotide sequence(s) 20, 20 are untagged primer nucleotide sequence(s).

Since this example of the quality control tracer 22C includes the fluorescent label 28 attached to a cleavable nucleobase, an exonuclease may be used to remove the fluorescent label 28 after the quality control method has been performed. In this example, the non-reactive nucleotide sequence 32' remains at least substantially intact after the quality control method has been performed, and thus the non-reactive nucleotide sequence 32' may be orthogonal to the primer nucleotide sequence(s) 20, 20' also attached to the gel material 24.

Moreover, since this example of the quality control tracer 22C also includes the excision site 30, enzymatic cleavage may be used to remove a cleavable portion 31' of the non-reactive sequence 32' after the quality control method has been performed. In this example, the cleavable portion 31' includes any sequence of oligonucleotides, the fluorescent label 28 attached to a nucleobase along the sequence, and the excision site 30. The portion 29' of the non-reactive nucleotide sequence 32' that remains attached to the gel material 24 after enzymatic cleavage is also a non-reactive nucleotide sequence, and thus will not participate in or interfere with a sequencing operation that is to be performed or is being performed. The remaining portion 29' may be a short poly T or poly A sequence, or may be a sequence that is orthogonal to the primer nucleotide sequence(s) 20, 20' also attached to the gel material 24.

The non-reactive nucleotide sequence 32' of FIG. 3C may include a functional group at its 5' end that is capable of attaching to the gel material 24. Examples of this functional group include an alkyne, a norbornyl (or other cycloalkenyls), a copper free click moiety (e.g., dibenzocyclooctyne (DIBO), other cycloalkynes, or others), and a thiol. This functional group may be selected based upon the gel material 24 that is used. For example, alkynes, norbornyls, and copper free click moieties may react with azides of PAZAM via click reactions, and thiols may react with SFA.

In this example, the fluorescent label 28 may be attached near (e.g., within 10 bases of) but not directly at, the 3' end of the sequence 32'. Any of the previously described fluorescent labels 28 may be used, as long as the selected label can covalently attach to a desirable nucleobase of the non-reactive nucleotide sequence 32'.

The quality control tracer 22C in FIG. 3C is used (e.g., in examples of the quality control method disclosed herein) in combination with separate primer nucleotide sequence(s) 20, 20'. Examples of suitable primer nucleotide sequence(s) 20, 20' include forward amplification primers or reverse amplification primers for hybridization to a complementary sequence and amplification of a sequence. Some specific examples of suitable primer nucleotide sequence(s) 20, 20' include the previously described P5 or P7 primers.

When the quality control tracer 22C in FIG. 3C is used, it is to be understood that it is present in a predetermined ratio with respect to the primer nucleotide sequence(s) 20, 20'. The predetermined ratio can be used in an example of the quality control method disclosed herein to indirectly determine the density and/or distribution of the primer nucleotide sequence(s) 20, 20'.

To form the example shown in FIG. 3C, sequential grafting or co-grafting may be used as previously described, except that the quality control tracer 22C is used instead of the quality control tracer 22A. In any of the grafting examples used to form the example shown in FIG. 3C, incubation takes place at a predetermined temperature which depends, in part, upon the quality control tracer 22C and the primer nucleotide sequence(s) 20, 20' used. Also in any of the grafting examples used to form the example shown in FIG. 3C, the solution may include the quality control tracer 22C and/or the primer nucleotide sequence(s) 20, 20', water, a buffer, and a catalyst. The quality control tracer 22C and/or the primer nucleotide sequence(s) 20, 20', whether present in the same solution/mixture or separate solutions/mixtures, may be present at any desired predetermined ratio.

Figure 3D:
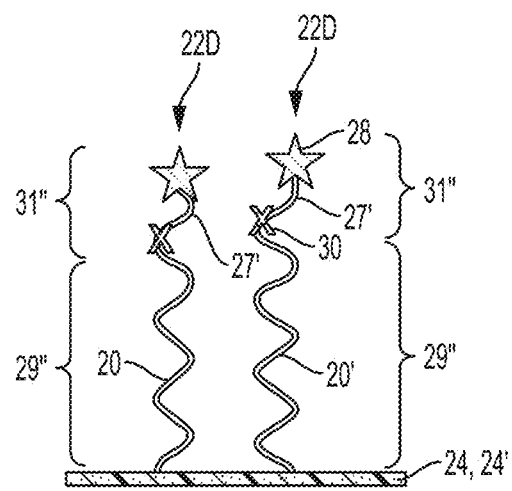

FIG. 3D depicts an example of the quality control tracer 22D that is included on the gel material 24/gel pad 24' without separate primer nucleotide sequence(s) 20, 20'. In this example, the quality control tracer 22D is a cleavable nucleotide sequence 27' tagged, at its 3' end, with the fluorescent label 28. The fluorescent label 28 may be any of the previously described fluorophores.

This example of the cleavable nucleotide sequence 27' includes a cleavable portion 31" and a remaining portion 29". The cleavable portion 31" includes the fluorescent label 28, any sequence of nucleotides, and an excision site 30 near the 3' end. The cleavable portion 31" may also include a functional group that attaches the fluorescent label 28 to the sequence of nucleotides. An example of this functional group is 5'-Dimethoxytrityl-5-[N-(trifluoroacetylamino-hexyl)-3-acrylimido]-2'-deoxyUridine,3'-[(2-cyanoethyl)-(N,N-diisopropyl)]-phosphoramidite (i.e., amino modifier C6 dT). Other examples include 5'-Dimethoxytrityl-N-dimethylformamidine-5-[N-(trifluoroacetylaminohexyl)-3-acrylimido]-2'-deoxyCytidine,3'-[(2-cyanoethyl)-(N,N-diisopropyl)]-phosphoramidite (amino modifier C6 dC) and the use of solid supports such as (2-Dimethoxytrityloxymethyl-6-fluorenylmethoxycarbonylamino-hexane-1-succinoyl)-long chain alkylamino-CPG. This functional group may be selected based upon the fluorescent label 28 that is used. The cleavable portion 31" of the cleavable nucleotide sequence 27' can be removed when the sequence 27' is exposed to an enzyme that targets the nucleotide located at the excision site 30.

The portion 29" of the cleavable nucleotide sequence 27' that remains attached to the gel material 24 after enzymatic cleavage is a primer nucleotide sequence 20, 20'. The primer nucleotide sequence 20, 20' that remains after the cleavable portion 31" is removed will participate in a sequencing operation that is to be performed or is being performed. Any example of the primer nucleotide sequence(s) 20, 20' disclosed herein may be used in the quality control tracer 22D.

The cleavable nucleotide sequence 27' of FIG. 3D may include a functional group at its 5' end that is capable of attaching to the gel material 24. Examples of this functional group include an alkyne, a norbornyl (or other cycloalkenyls), a copper free click moiety (e.g., dibenzocyclooctyne (DIBO), other cycloalkynes, or others), and a thiol. This functional group may be selected based upon the gel material 24 that is used. For example, alkynes, norbornyls, and copper free click moieties may react with azides of PAZAM via click reactions, and thiols may react with SFA.

An example of the P5 primer tagged, at its 3' end, with the fluorescent label, TEXAS RED®, is:

```
                                          (SEQ. ID NO. 24)
5'-alkyne-AATGATACGGCGACCACCGAGAUCTACA

[Amino C6 dT-Texas Red]-3'
```

The quality control tracer 22D in FIG. 3D can be used in an example of the quality control method disclosed herein to directly determine the density and/or distribution of the primer nucleotide sequence(s) 20, 20' that is part of the tracer 22D.

To form the example shown in FIG. 3D, grafting of one type of quality control tracer 22D (each of which includes the same primer nucleotide sequence(s) 20 or 20') may be used, or co-grafting of different types of quality control tracers 22D (e.g., some of which include the primer nucleotide sequence 20 and others of which include a different primer nucleotide sequence 20') may be used. Grafting or co-grafting may be performed as previously described, except that the quality control tracer 22D is used instead of the quality control tracer 22A.

Figure 4:
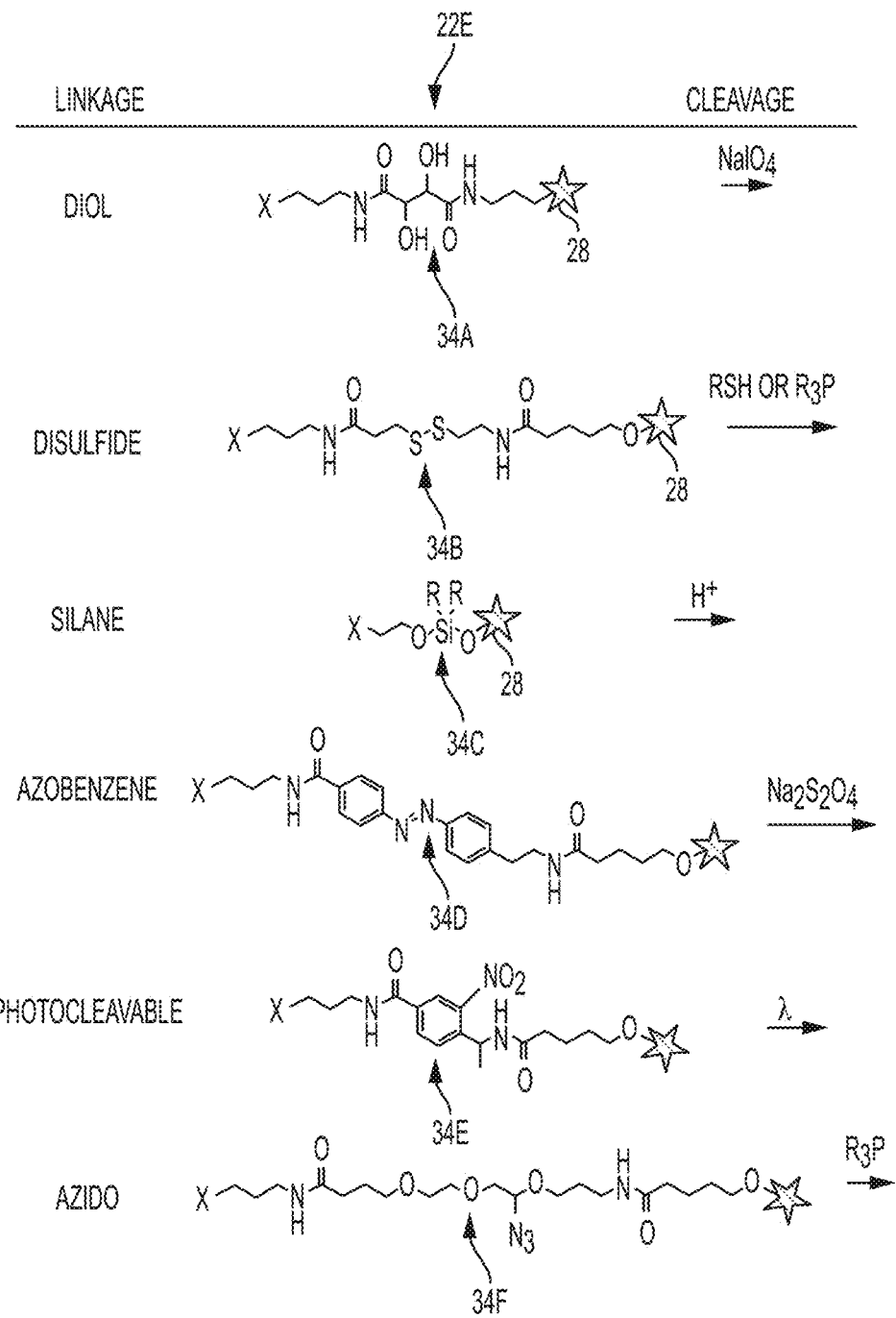
FIG. 4 depicts several examples of quality control tracers including a linker molecule and examples of chemicals that may be used to cleave the linker molecule.

Still other examples of the quality control tracer 22E are shown in FIG. 4. In these examples, the quality control tracer 22E is a cleavable nucleotide sequence tagged, at its 3' end, with the fluorescent label 28. Each of these examples of the cleavable nucleotide sequence includes a nucleotide sequence X, a linker molecule 34, and the fluorescent label 28.

The nucleotide sequence X may be a non-reactive nucleotide sequence (such as sequence 32) or a primer nucleotide sequence (such as sequence 20 or 20'). When the nucleotide sequence X is the non-reactive nucleotide sequence, the quality control tracer 22E may be used in combination with separate primer nucleotide sequence(s) 20, 20' (similar to the examples shown in FIGS. 3A through 3C. When the nucleotide sequence X is the primer nucleotide sequence, the quality control tracer 22E may be used alone (i.e., without separate primer nucleotide sequence(s) 20, 20') (similar to the example shown in FIG. 3D).

The nucleotide sequence X of FIG. 4 may include a functional group at its 5' end that is capable of attaching to the gel material 24. Examples of this functional group include an alkyne, a norbornyl (or other cycloalkenyls), a copper free click moiety (e.g., dibenzocyclooctyne (DIBO), other cycloalkynes, or others), and a thiol. This functional group may be selected based upon the gel material 24 that is used. For example, alkynes, norbornyls, and copper free click moieties may react with azides of PAZAM via click reactions, and thiols may react with SFA.

The linker molecule 34 includes, at one end, a functional group that can attach (directly or indirectly) to the fluorescent label 28 and, at the other end, a functional group that can attach (directly or indirectly) to the nucleotide sequence X (e.g., at the 3' end or at a particular nucleobase in the sequence X). The linker molecule 34 of the quality control tracer 22E provides a chemical linkage that can undergo a cleavage reaction that removes at least the fluorescent label 28 from the quality control tracer 22E after an example of the quality control method has been performed. The cleavage reaction that is performed depends upon the linker molecule 34 that is used. Example linker molecules 34 include a diol, a disulfide, a silane, an azobenzene, a photocleavable group, and an azido.

A diol is any chemical compound containing two hydroxyl groups. Linear or cyclic diols may be used.

Examples of suitable diols are vicinal diols, where the hydroxyl groups are attached to adjacent carbon atoms. Vicinal diols are cleavable under oxidative conditions, such as exposure to periodate (such as sodium periodate) or under enzymatic conditions. An example of a suitable diol is the tartaric acid-derived diol shown as 34A in FIG. 4. In this example, the amine groups at each end of the diol attach to respective moieties, one of which is attached to the 3' end of nucleotide sequence X and the other of which is attached to the fluorescent label 28 via any suitable attachment site (e.g., alcohol, amine, carboxylic acid). The diol may be cleaved by exposing the quality control tracer 22E to sodium periodate ($NaIO_4$) which can oxidatively cleave the diol into two aldehydes.

A disulfide has the general structure $R^1$—S—S—$R^2$, where $R^1$ and $R^2$ may be any of alkyl or aryl groups. Disulfide bonds are cleaved under reducing conditions. An example of a suitable disulfide is shown as 34B in FIG. 4. In this example, the amine group at one end of the disulfide is attached via a linker such as an alkyl chain to the nucleotide sequence X at the 3' end and the amine group at the other end of the disulfide forms an amido linkage

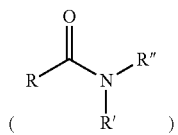

where R is —$(CH_2)_4$—O-fluorescent label 28, R' is H, and R" is —$(CH_2)_2$—S—S—$(CH_2)_2$—(C=O)—NH—$(CH_2)_3$—X. The fluorescent label 28 is attached via any suitable attachment site (e.g., alcohol, amine, carboxylic acid). In an example, the disulfide may be cleaved by exposing the quality control tracer 22E to reducing conditions, such as a thiol ($R^3SH$, where $R^3$ is may be any suitable alkyl group) or a tertiary phosphine ($R^4_3P$, where $R^4$ is any suitable alkyl group). The reaction of the thiol with the disulfide will break the disulfide bond and create a new disulfide and a thiol derived from the original disulfide. The reaction of the tertiary phosphine with the disulfide is a bimolecular nucleophilic substitution ($S_N2$) reaction that will break the disulfide bond and create two sulfur-containing products.

A silane, as used herein and as shown at 34C in FIG. 4, includes a silicon atom bonded to two oxygen atoms and two R groups (e.g., each of which may be alkyl or aryl groups). In this example, the oxygen atoms of the silane attach, respectively, to a linker such as an alkyl chain which is attached to the nucleotide sequence X at the 3' end and to the fluorescent label 28 via any suitable attachment site (e.g., alcohol, amine, carboxylic acid). The silane may be cleaved at one of the Si—O bonds by exposing the quality control tracer 22E to an acid (shown as $H^+$ in FIG. 4) or by treatment with fluoride ion (not shown in FIG. 4).

An azobenzene is a chemical compound composed of two phenyl rings linked by a N=N double bond. Different functional groups may extend from the phenyl rings at the para positions relative to the N=N double bond. These functional groups may be the same or different, and examples include an amido group, an alkyl amine, or hydroxyl groups. An example of a suitable azobenzene is shown as 34D in FIG. 4. In this example, the functional groups include an amido group and ethylamine. The amido group is attached to a linker such as an alkyl chain which is attached to the nucleotide sequence X at the 3' end, and the amine group of the ethylamine forms an amido linkage

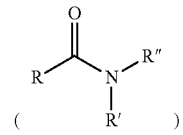

where R is —$(CH_2)_4$—O-fluorescent label 28, R' is H, and R" is —$(CH_2)_2$-azobenzene-(C=O)—NH—$(CH_2)_3$—X. The fluorescent label 28 is attached via any suitable attachment site (e.g. alcohol, amine, carboxylic acid). In an example, the azobenzene may be cleaved by exposing the quality control tracer 22E to sodium dithionate ($Na_2S_2O_4$). The reaction of the sodium dithionate with the azobenzene reduces the azobenzene to two aniline groups.

A photocleavable group is a non-nucleotide moiety that includes a photo cleavage site, where cleavage occurs by irradiation with a predetermined wavelength of light for a predetermined time. The photocleavable group can be used as an intermediary to attach any available phosphoramidite modification at the 3' end of the nucleotide sequence X to a functional group attached to the fluorescent label 28. An example of a suitable photocleavable group, an ortho-nitrobenzyl group, is shown as 34E in FIG. 4. In this example, photocleavable group includes amine groups at either end. In this example, the amine group at one end of the photocleavable group is attached to a linker such as an alkyl chain which is attached to the nucleotide sequence X, and the amine group at the other end of the disulfide forms an amido linkage attached to the fluorescent label 28 through —$(CH_2)_4$—O—. The fluorescent label 28 is attached via any suitable attachment site (e.g. alcohol, amine, carboxylic acid). In an example, at least the fluorescent label 28 is cleaved from the quality control tracer 22E at the photocleavable site by exposing the quality control tracer 22E to light of a predetermined wavelength for a predetermined time.

As mentioned herein, an azido is any molecule including the group $N_3$. An example of a suitable azido is shown as the O-azidoalkyl group 34F in FIG. 4. In this example, the amine group at one end of the azido is attached to a linker such as an alkyl chain which is attached to the nucleotide sequence X at the 3' end, and the amine group at the other end of the azido forms an amido linkage

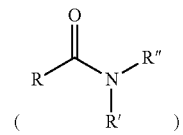

where (in this example) R is —$(CH_2)_4$—O-fluorescent label 28, R' is H, and R" is —$(CH_2)_3$—O—$(CN_3)$—$(CH_2)$—(O $(CH_2)_2)_2$—$(CH_2)$—(C=O)—NH—$(CH_2)_3$—X. The fluorescent label 28 is attached via any suitable attachment site (e.g. alcohol, amine, carboxylic acid). In an example, the azido may be cleaved by exposing the quality control tracer 22E to a tertiary phosphine ($R^6_3P$, where $R^6$ is an appropriately substituted alkyl or aryl group). The tertiary phosphine and the azido undergo the Staudinger reduction reaction.

Each of the linker molecules 34 disclosed herein can undergo a chemical cleavage reaction that removes at least the fluorescent label 28 from the quality control tracer 22E after an example of the quality control method has been performed. The remaining portion may be a non-reactive nucleotide sequence (that will not participate in sequencing) or a primer nucleotide sequence (that will participate in sequencing).

When the nucleotide sequence X of the quality control tracer 22E is non-reactive, the quality control tracer 22E may be sequentially grafted or co-grafted with separate primer nucleotide sequence(s) 20, 20' as previously described herein. When the nucleotide sequence X of the quality control tracer 22E is a primer nucleotide sequence(s) 20, 20', one type of quality control tracer 22E (each of which includes the same primer nucleotide sequence(s) 20 or 20') may be grafted, or different types of quality control tracers 22E (e.g., some of which include the primer nucleotide sequence 20 and others of which include a different primer nucleotide sequence 20') may be co-grafted. Grafting or co-grafting may be performed as previously described, except that an example of the quality control tracer 22E is used instead of the quality control tracer 22A.

Referring back to FIG. 2D, an example of the as-grafted quality control tracer(s) 22 with separate primer nucleotide sequence(s) 20, 20' is depicted. In examples of the tracer 22 that include the primer nucleotide sequence(s) 20, 20' (e.g., tracer 22D and some examples of tracer 22E), separate primer nucleotide sequence(s) 20, 20' will not be present with the tracer(s) 22.

Figure 5:
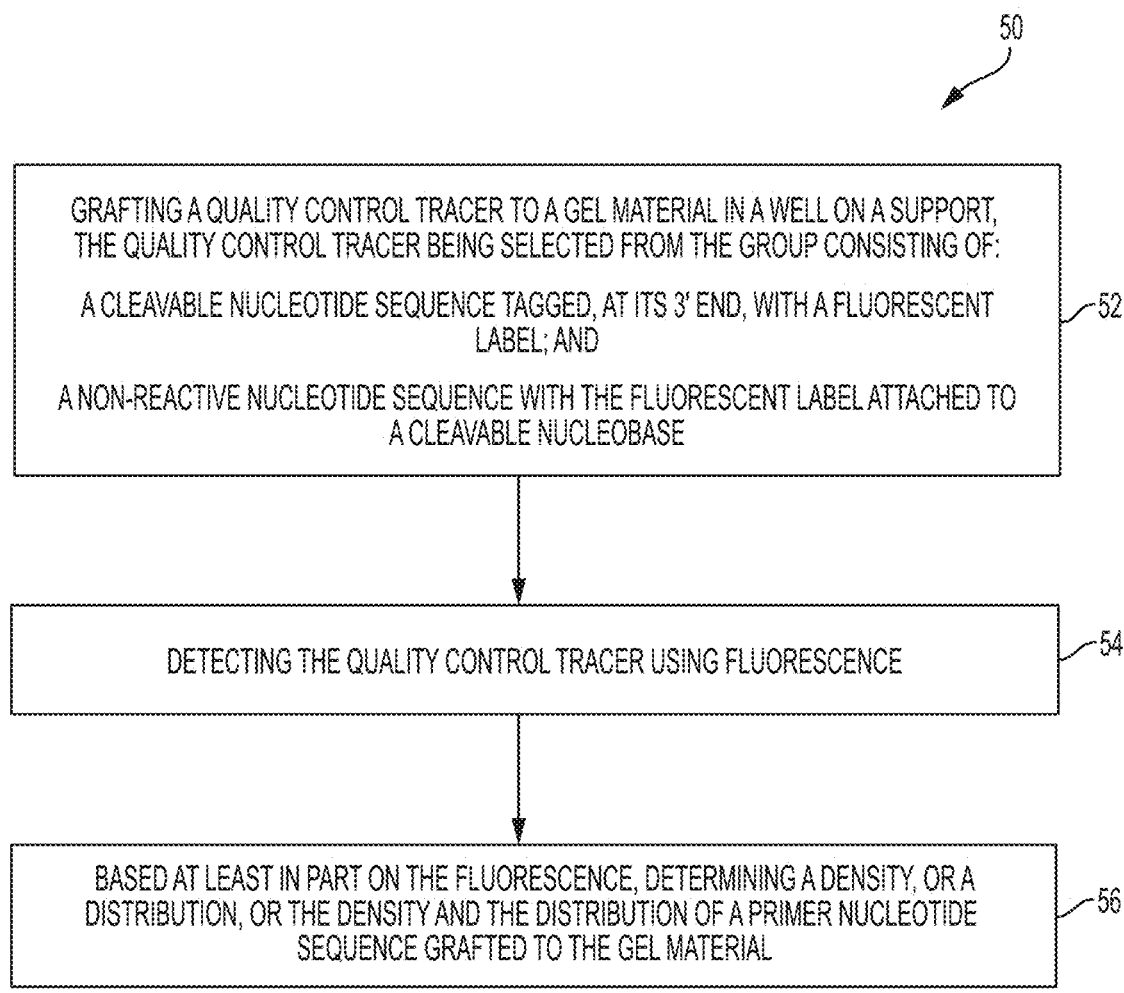
FIG. 5 is a flow diagram depicting an example of a quality control method.

The array 10 disclosed herein may be used in a quality control method. An example of the quality control method is depicted in FIG. 5. The method 50 generally includes grafting a quality control tracer 22 to a gel material 24 in a well 16' on a support 12, the quality control tracer being selected from the group consisting of a cleavable nucleotide sequence 27, 27' tagged, at its 3' end, with a fluorescent label 28 and a non-reactive nucleotide sequence 32, 32' with the fluorescent label 28 attached to a cleavable nucleobase (as shown at reference numeral 52); detecting the quality control tracer 22 using fluorescence (as shown at reference numeral 54); and based at least in part on the fluorescence, determining a density, or a distribution, or the density and the distribution, of a primer nucleotide sequence 20, 20' grafted to the gel material 24 (as shown at reference numeral 56).

The quality control method may be performed after the quality control tracer 22, alone or in combination with separate primer nucleotide sequence(s) 20, 20', is/are grafted to the gel material 24 and prior to completion of flow cell manufacturing (e.g., prior to the bonding of the array 10 to a top substrate flow cell). The quality control method may also or alternatively be performed by an end-user of the fully manufactured flow cell. When the quality control method is performed by the end-user of the flow cell, it is to be understood that the method may be performed prior to loading any sequencing workflow reagents and DNA sample onto the flow cell. Because each quality control tracer 22A, 22B, 22C, 22D, 22E includes the detectable fluorescent label 28, hybridization of fluorescently-labeled complementary nucleotides does not need to be performed as part of the quality control method disclosed herein.

In the method 50, the grafting of the various examples of the quality control tracer 22A, 22B, 22C, 22D, 22E may be accomplished as previously described.

Each of the example quality control tracers 22A, 22B, 22C, 22D, 22E includes the fluorescent label 28, which will emit light of longer wavelength(s) when exposed to incident radiation of shorter wavelength(s). As such, detecting the quality control tracer 22 may be accomplished by exposing the array 10 (or flow cell including the array 10) to radiation emitted by a laser. After laser excitation, the emitted fluorescence (in terms of intensity) from the fluorescent label 28 of each quality control tracer 22A, 22B, 22C, 22D, 22E is captured via a suitable fluorescence detector.

When the quality control tracer 22A, 22B, 22C, or some examples of tracer 22E are utilized in a predetermined ratio with separate primer nucleotide sequence(s) 20, 20', the fluorescence intensity from these quality control tracers 22A, 22B, 22C, 22E and the predetermined ratio may be used to assess or indirectly determine the density and/or distribution of the primer nucleotide sequence(s) 20, 20'. The fluorescence intensity indicates the density and/or distribution of the quality control tracers 22A, 22B, 22C, 22E, and the predetermined ratio enables the data for the quality control tracers 22A, 22B, 22C, 22E to be correlated to the primer nucleotide sequence(s) 20, 20'.

When the quality control tracer 22D or other examples of tracer 22E (which include primer nucleotide sequence(s) 20, 20') are utilized, the fluorescence results alone may be used to assess or directly determine the density and/or distribution of the primer nucleotide sequence(s) 20, 20'. These examples of the quality control tracer 22D, 22E include the sequences 20, 20' as part of the tracer 22D, 22E, and thus the fluorescence intensity alone indicates the density and/or distribution of the primer nucleotide sequence(s) 20, 20'.

After completion of the quality control method (e.g., at the end-user portion of the workflow), the fluorescent label 28 may be cleaved from quality control tracers 22A, 22B, 22C, 22D, 22E using the methods described herein.

As mentioned above in reference to FIG. 3A, quality control tracer 22A includes the excision site 30. As such, cleavage of the fluorescent label 28 in this example tracer 22A may be accomplished via enzymatic cleavage. The quality control tracer 22A is exposed to an enzyme that targets the nucleotide located at the excision site 30. The enzyme may be introduced prior to initiating sequencing, or may be introduced as part of a cluster generation process of a sequencing workflow. Examples of suitable enzymes include exonucleases (which remove successive nucleotides from an end of the sequence), endonucleases (which cleave phophodiester bonds within a sequence), base excision repair enzymes (which remove specific bases to form an apurinic/apyrimidinic (AP) site, which can then be cleaved by an AP endonuclease), restriction enzymes (which scan the quality control tracer 22A for a particular sequence of 4 to 6 nucleotides at which to cut the single-stranded sequence), etc. Some specific examples are shown in Table 1 below.

TABLE 1

| Enzyme | QC Tracer | Cleavage |
| --- | --- | --- |
| USER enzyme | 5'-NNNNUNNNN-*- 3' | Before read 1 of sequencing workflow |
| FPG (formamido pyrimidine DNA glycosylase) | 5'-NNNN(oxo-G) NNNN-*-3' | Before read 1 or read 2 of sequencing workflow |

In Table 1, *represents the fluorescent label 28, N represents nucleotides, and the excision site is in bold.

In one example in Table 1, the excision site 30 is a uracil (dU) that is targeted by the USER enzyme. The USER enzyme is a mixture of uracil DNA glycosylase (UDG) and the DNA glycosylase-lyase endonuclease VIII. UDG catalyzes the excision of the uracil base, forming an abasic (apyrimidinic) site while leaving the phosphodiester backbone intact. The lyase activity of endonuclease VIII breaks the phosphodiester backbone at the 3' and 5' sides of the abasic site so that base-free deoxyribose is released. As such, cleavage of tracer 22A at excision site 30 removes a portion 31 of the sequence 27 and the fluorescent label 28 from the support 12. In the other example in Table 1, the excision site 30 is an oxidized purine (e.g., oxoG) that is targeted by FPG. FPG recognizes and removes the oxidized guanine. The FPG acts as both an N-glycosylase and an AP-lyase.

The portion 29 of the quality control tracer 22A that remains attached to the gel material 24 after enzymatic cleavage is a non-reactive nucleotide sequence, and thus will not participate in or interfere with a sequencing operation that is to be performed or is being performed.

As mentioned above in reference to FIG. 3B, quality control tracer 22B includes fluorescent label 28 attached to a cleavable nucleobase of the sequence 32. The quality control tracer 22B is exposed to an exonuclease that catalyzes the excision of the particular base by phosphodiester cleavage. The exonuclease may be introduced prior to initiating sequencing, or may be introduced as part of a cluster generation process of a sequencing workflow. As an example, Exonuclease I catalyzes the excision of a uracil base having the fluorescent label 28 attached thereto.

The sequence 32 of the quality control tracer 22B that remains attached to the gel material 24 after nucleobase cleavage is non-reactive, and thus will not participate in or interfere with a sequencing operation that is to be performed or is being performed.

As mentioned above in reference to FIG. 3C, quality control tracer 22C includes the fluorescent label 28 attached to a cleavable nucleobase of the sequence 32' as well as the excision site 30. As such, cleavage of the fluorescent label 28 in this example tracer 22C may be accomplished via any of the previously described examples of enzymatic cleavage. In one example, an exonuclease may be used to catalyze the excision of the base having the fluorescent label 28 attached thereto. In another example, an enzyme that targets the nucleotide located at the excision site 30 may be used to catalyze the excision of the portion 31' of the sequence 32'. In these examples, the enzyme may be introduced prior to initiating sequencing, or may be introduced as part of a cluster generation process of a sequencing workflow.

The portion 29' of the sequence 32' of the quality control tracer 22C that remains attached to the gel material 24 after nucleobase or portion 31' cleavage is non-reactive, and thus will not participate in or interfere with a sequencing operation that is to be performed or is being performed.

As mentioned above in reference to FIG. 3D, quality control tracer 22D includes the excision site 30. As such, cleavage of the fluorescent label 28 in this example tracer 22D may be accomplished via any of the previously described examples of enzymatic cleavage. In this example, the portion 29" of the sequence 27' that remains attached to the gel material 24 after portion 31" cleavage is a primer nucleotide sequence 20, 20', and thus will participate in a sequencing operation that is to be performed or is being performed.

As mentioned above in reference to FIG. 4, the various examples of the quality control tracer 22E include the linker molecule 34. Cleavage of the fluorescent label 28 in these example tracers 22E may be accomplished via chemical cleavage by exposing the tracer 22E to a chemical that is suitable for cleaving the linker molecule 34 present in the tracer 22E. Various examples of the linker molecules 34A, 34B, 34C, 34D, 34E, 34F and associated cleavage chemicals are described in reference to FIG. 4. In these examples, the cleavage chemical may be introduced prior to initiating sequencing.

The portion of the quality control tracer 22E that remains attached to the gel material 24 after chemical cleavage will depend upon the nucleotide sequence X and where the chemical cleavage takes place. The remaining portion may include a non-reactive nucleotide sequence (which will not participate or interfere with sequencing) or a primer nucleotide sequence (which will participate in sequencing).

While not shown in the figures, another example of the method includes incorporating an example of the quality control tracer (e.g., 22A, 22B, 22C, and some examples of 22E) into a grafting mix with a primer nucleotide sequence 20, 20' at a predetermined ratio; exposing the grafting mix to a gel material 24 in a well 16' on a support 23; incubating the grafting mix, thereby co-grafting the quality control tracer 22A, 22B, 22C, and some examples of 22E and the primer nucleotide sequence 20, 20' to the gel material 24; detecting the quality control tracer using fluorescence; and based at least in part on the fluorescence and the predetermined ratio, determining a density, or a distribution, or the density and the distribution, of the primer nucleotide sequence 20, 20' grafted to the gel material 24.

A variety of sequencing approaches or technologies, including techniques often referred to as sequencing-by-synthesis (SBS), sequencing-by-ligation, pyrosequencing, and so forth may be performed after the fluorescent label 28 is cleaved. With any of these techniques, since the gel material 24 and attached primer nucleotide sequences 20, 20' are present in the sites 16 and not on the interstitial regions 18, amplification will be confined to the various sites 16.

Briefly, a sequencing by synthesis (SBS) reaction may be run on a system such as the HISEQ®, HISEQX®, MISEQ® or NEXTSEQ® sequencer systems from Illumina (San Diego, CA). A set of target DNA molecules to be sequenced is hybridized to the bound primer nucleotide sequences 20, 20' (and not to any non-reactive nucleotide sequences) and then amplified by bridge amplification or by kinetic exclusion amplification. Denaturation leaves single-stranded templates anchored to the gel material 24, and several million dense clusters of double-stranded DNA are generated (i.e., cluster generation). The sequencing reactions are then carried out. The data area aligned and compared to a reference, and sequencing differences are identified.

To further illustrate the present disclosure, an example is given herein. It is to be understood that this example is provided for illustrative purposes and is not to be construed as limiting the scope of the present disclosure.

EXAMPLE

The following quality control tracer was used:

```
                                           (SEQ. ID NO. 25)
5'-Hexyne-poly T tail-CATCTAGGCATCTAAGCATCAA UCTTACA[Amino C6 dT-Texas Red]-3'
```

To evaluate an example of the QC tracer for quality control of P5/P7 primer grafting onto a substrate surface, P5/P7 primer grafting mixes were prepared with a 10% spike of a QC tracer and without the QC tracer spike (control). Substrate surfaces grafted with the P5/P7 primer mix that included the 10% spike of QC tracer were evaluated by measuring tracer fluorescence. The control surfaces (without QC tracer spike) were evaluated by hybridization-based TET QC. TET is a dye labeled oligonucleotide having complementary sequence to the P5/P7 primers. TET is hybridized to the P5/P7 primers on a surface, the excess TET is washed away, and the attached dye concentration is measured by fluorescence detection.

Figure 6A:
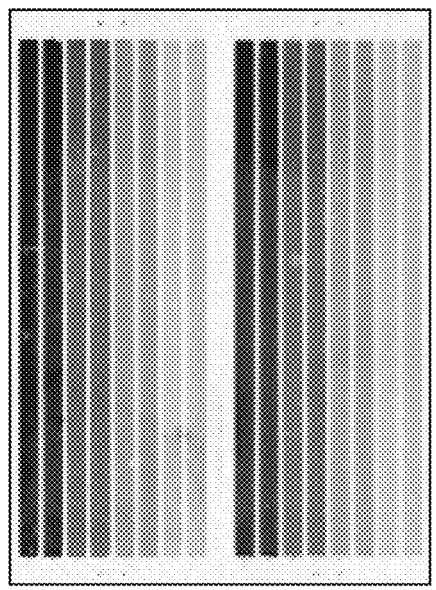
FIGS. 6A and 6B are, respectively, a fluorescence image of a control flow cell grafted with primers and hybridized with complementary dye-containing oligonucleotides (TET QC) and a fluorescence image of flow cells grafted with an example of the quality control tracer disclosed herein.
Figure 6B:
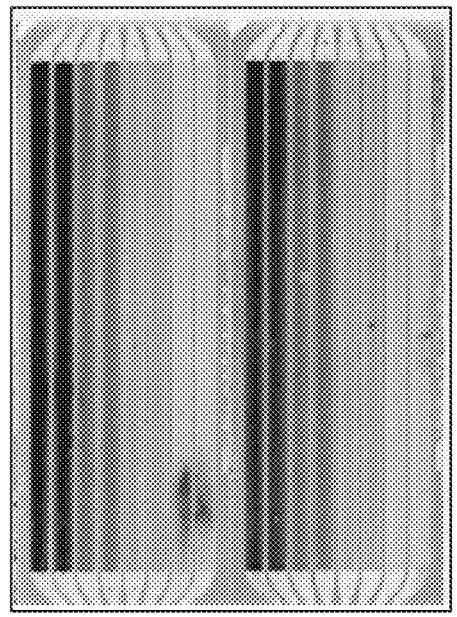
Figure 6C:
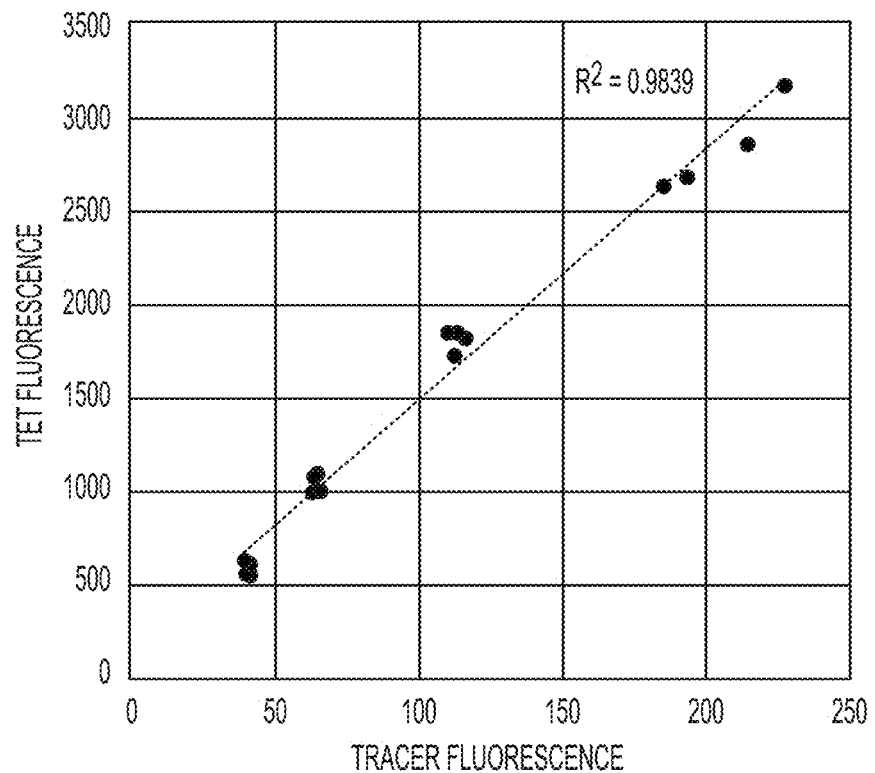
FIG. 6C is a graph depicting quality control tracer fluorescence versus TET fluorescence for the grafted surfaces of FIGS. 5A and 5B.

FIGS. 6A and 6B respectively show a fluorescence image of grafted control substrate surfaces hybridized with complementary dye-containing oligonucleotides (TET QC) and a fluorescence image of grafted substrate surfaces that include QC tracers. FIG. 6C shows a plot of QC tracer fluorescence versus TET fluorescence for the grafted surfaces of FIGS. 6A and 6B. The data in FIGS. 6A-6C show that fluorescence intensity from the QC tracer correlates with P5/P7 density on the substrate surface.

To evaluate cleavage of grafted QC tracers from the surface of a flow cell during a standard cluster generation process, flow cells grafted with different QC tracers were used. FIG. 7A shows an initial fluorescence image, which shows flow cells grafted with QC tracers before cluster generation. FIG. 7B shows a post-clustering fluorescence image, which shows flow cells grafted with QC tracers after cluster generation. The QC tracers (at 200 nM) were:

```
(SEQ. ID NO. 25)  (200 nM TRACER)
5'-Hexyne-poly T tail-CATCTAGGCATCTAAGCATCA AUCTTACA[Amino C6 dT-Texas Red]-3'

(SEQ. ID NO. 26)  (200 nM P5)
5'-Hexyne-poly T tail-AATGATACGGCGACCACCGAG

AUCTACA[Amino C6 dT-Texas Red]-3'
and (SEQ. ID NO. 26) with a corrected final
P5/P7 ratio of 1:1.  (200 nM Pg (1:1))
5'-Hexyne-poly T tail-AATGATACGGCGACCACCGAG AUCTACA[Amino C6 dT-Texas Red]-3'
```

Referring to the initial fluorescence image of FIG. 7A, the dark areas in the flow cells are the signal from the QC tracers; lighter areas are control lanes (i.e., no QC tracers were present). Referring to post-clustering fluorescence image of FIG. 7B, the signal from the QC tracers is substantially reduced indicating cleavage of the QC tracers during cluster formation.

FIGS. 8A and 8B show a plot of QC tracer fluorescence post-grafting and a plot of QC tracer fluorescence post-clustering, respectively, for the grafted flow cells of FIGS. 7A and 7B. The data show that residual fluorescence after cluster formation is minimal. The cleavage efficiency ranges from about 97% to about 99%.

To evaluate the effect of QC tracer grafting and subsequent cleavage on downstream sequencing metrics, the flow cells of FIGS. 7A and 7B were used for sequencing.

FIGS. 9A and 9B show a plot of the read 1 (R1) fluorescence intensity and a plot of the read 2 (R2) fluorescence intensities, respectively, for the red channel after one sequencing cycle (C1). The data show that the C1 intensities in the red channel are minimally impacted by the use of QC tracers.

FIGS. 10A and 10B show a plot of the read 1 (R1) fluorescence intensity and a plot of the read 2 (R2) fluorescence intensities, respectively, for the green channel after one sequencing cycle (C1). The data show that the C1 intensities in the green channel are minimally impacted by the use of QC tracers.

FIGS. 11A and 11B show a plot of read 1 (R1) sequence alignment and plot of read 2 (R2) sequence alignment, respectively, to a reference genome. The data show that there is little or no impact by the use of QC tracers on sequence alignment metrics.

FIGS. 12A and 12B show a plot of read 1 (R1) sequencing error rates and plot of read 2 (R2) sequencing error rates, respectively. The data show that there is little or no impact by the use of QC tracers on sequencing error rate metrics.

Additional Notes

It should be appreciated that all combinations of the foregoing concepts (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

All publications, patents, and patent applications cited in this Specification are hereby incorporated by reference in their entirety.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

It is to be understood that the ranges provided herein include the stated range and any value or sub-range within the stated range. For example, a range from about 10 kDa to about 1500 kDa, should be interpreted to include not only the explicitly recited limits of from about 10 kDa to about 1500 kDa, but also to include individual values, such as about 18 kDa, about 325 kDa, about 425 kDa, about 1075.5 kDa, etc., and sub-ranges, such as from about 425 kDa to about 990 kDa, from about 235 kDa to about 780 KDa, etc. Furthermore, when "about" and/or "substantially" are/is utilized to describe a value, they are meant to encompass minor variations (up to +/−10%) from the stated value.

While several examples have been described in detail, it is to be understood that the disclosed examples may be modified. Therefore, the foregoing description is to be considered non-limiting.

What is claimed is:

1. A method of determining the density, the distribution, or the density and the distribution of an untagged primer nucleotide sequence grafted to a support comprising:
   providing the support comprising:
     a plurality of discrete wells;
     a gel material positioned in each of the plurality of discrete wells;
     a quality control tracer grafted to the gel material in each of the plurality of discrete wells; and
     the untagged primer nucleotide sequence grafted to the gel material in each of the plurality of discrete wells;
   wherein the quality control tracer comprises:
     a cleavable nucleotide sequence comprising a remaining portion and a cleavable portion, the remaining portion being a non-reactive nucleotide sequence having a first end grafted to the gel material and a second end linked to the cleavable portion, and the cleavable portion including a cleavage site; and
   a detectable label attached to a 3' end of the cleavable nucleotide sequence;
   the cleavable nucleotide sequence being selected from the group consisting of
     5'-CATCTAGGCATCTAAGCATCAAUCTTACA-3' (SEQ. ID NO. 3),
     5'-polyT-CATCTAGGCATCTAAGCATCAAUCT-TACA-3' (SEQ. ID NO. 6),
     5'-alkyne-CATCTAGGCATCTAAGCATCAAUCT-TACA-3' (SEQ. ID NO. 9),
     5'-(alkyne)-(polyT or TTTTTT)AATGATACGGCGAC-CACCGAGAUCACAC-3' (SEQ. ID NO. 19); and
   wherein the quality control tracer and the untagged primer nucleotide sequence are grafted to the gel material in a predetermined ratio;
   detecting a signal from the detectable label; determining the density and/or distribution of the quality control tracer based at least in part on the signal from the detectable label; and
   determining the density and/or distribution of the grafted untagged primer nucleotide sequence based on the signal from the detectable label and the predetermined ratio.

2. The method of claim 1, wherein prior to providing the support, the method further comprises grafting the quality control tracer to the gel material.

3. The method of claim 2, wherein prior to providing the support, the method further comprises grafting the untagged primer nucleotide sequence to the gel material, either before or at the same time as the grafting of the quality control tracer.

4. The method of claim 1, further comprising removing the detectable label from the quality control tracer by a cleavage reaction at the cleavage site.

5. The method of claim 4, wherein the removing is accomplished by enzymatic cleavage or chemical cleavage.

6. The method of claim 1, wherein the detectable label is a fluorescent label and the detected signal is fluorescence.

7. The method of claim 6, wherein the fluorescent label is a sulfonyl chloride dye, a cyanine dye, a xanthene fluorophore, or an indocarboeyanine dye.

* * * * *

UNITED STATES PATENT AND TRADEMARK OFFICE
CERTIFICATE OF CORRECTION

PATENT NO. : 11,952,619 B2  
APPLICATION NO. : 16/868308  
DATED : April 9, 2024  
INVENTOR(S) : Peyton Shieh et al.

Page 1 of 1

It is certified that error appears in the above-identified patent and that said Letters Patent is hereby corrected as shown below:

On the Title Page

In the right-hand column, item (56) under "OTHER PUBLICATIONS", delete "orthogona" and insert -- orthogonal --.

In the Claims

Column 47, Line 38, in Claim 1, after "(SEQ ID NO. 9)," insert -- and --.

Column 48, Line 39, in Claim 7, delete "indocarboeyanine" and insert -- indocarbocyanine --.

Signed and Sealed this  
Eighth Day of October, 2024

Katherine Kelly Vidal  
*Director of the United States Patent and Trademark Office*

SEQUENCE LISTING

<160> NUMBER OF SEQ ID NOS: 26

<210> SEQ ID NO 1
<211> LENGTH: 29
<212> TYPE: DNA

```
<213> ORGANISM: Artificial Sequence
<220> FEATURE:
<223> OTHER INFORMATION: synthesized

<400> SEQUENCE: 1
aatgatacgg cgaccaccga gauctacac                                    29

<210> SEQ ID NO 2
<211> LENGTH: 24
<212> TYPE: DNA
<213> ORGANISM: Artificial Sequence
<220> FEATURE:
<223> OTHER INFORMATION: synthesized
<220> FEATURE:
<221> NAME/KEY: misc_feature
<222> LOCATION: (22)..(22)
<223> OTHER INFORMATION: 8-oxo-guanine

<400> SEQUENCE: 2
caagcagaag acggcatacg anat                                         24

<210> SEQ ID NO 3
<211> LENGTH: 29
<212> TYPE: DNA
<213> ORGANISM: Artificial Sequence
<220> FEATURE:
<223> OTHER INFORMATION: synthesized

<400> SEQUENCE: 3
catctaggca tctaagcatc aaucttaca                                    29

<210> SEQ ID NO 4
<211> LENGTH: 27
<212> TYPE: DNA
<213> ORGANISM: Artificial Sequence
<220> FEATURE:
<223> OTHER INFORMATION: synthesized

<400> SEQUENCE: 4
acatacatac atacatacau acataca                                      27

<210> SEQ ID NO 5
<211> LENGTH: 26
<212> TYPE: DNA
<213> ORGANISM: Artificial Sequence
<220> FEATURE:
<223> OTHER INFORMATION: synthesized

<400> SEQUENCE: 5
attgattgat tgattgatug attgat                                       26

<210> SEQ ID NO 6
<211> LENGTH: 49
<212> TYPE: DNA
<213> ORGANISM: Artificial Sequence
<220> FEATURE:
<223> OTHER INFORMATION: synthesized
<220> FEATURE:
<221> NAME/KEY: misc_feature
<222> LOCATION: (1)..(20)
<223> OTHER INFORMATION: present or absent Thymine base

<400> SEQUENCE: 6
nnnnnnnnnn nnnnnnnnnn catctaggca tctaagcatc aaucttaca              49

<210> SEQ ID NO 7
<211> LENGTH: 47
```

```
<212> TYPE: DNA
<213> ORGANISM: Artificial Sequence
<220> FEATURE:
<223> OTHER INFORMATION: synthesized
<220> FEATURE:
<221> NAME/KEY: misc_feature
<222> LOCATION: (1)..(20)
<223> OTHER INFORMATION: present or absent Thymine base

<400> SEQUENCE: 7
nnnnnnnnnn nnnnnnnnnn acatacatac atacatacau acataca        47

<210> SEQ ID NO 8
<211> LENGTH: 46
<212> TYPE: DNA
<213> ORGANISM: Artificial Sequence
<220> FEATURE:
<223> OTHER INFORMATION: synthesized
<220> FEATURE:
<221> NAME/KEY: misc_feature
<222> LOCATION: (1)..(20)
<223> OTHER INFORMATION: present of absentThymine base

<400> SEQUENCE: 8
nnnnnnnnnn nnnnnnnnnn attgattgat tgattgatug attgat        46

<210> SEQ ID NO 9
<211> LENGTH: 29
<212> TYPE: DNA
<213> ORGANISM: Artificial Sequence
<220> FEATURE:
<223> OTHER INFORMATION: synthesized
<220> FEATURE:
<221> NAME/KEY: misc_feature
<222> LOCATION: (29)..(29)
<223> OTHER INFORMATION: red fluorescent dye attached to Adenine through
      Amino-modifier C6 dT linker

<400> SEQUENCE: 9
catctaggca tctaagcatc aaucttaca                            29

<210> SEQ ID NO 10
<211> LENGTH: 27
<212> TYPE: DNA
<213> ORGANISM: Artificial Sequence
<220> FEATURE:
<223> OTHER INFORMATION: synthesized
<220> FEATURE:
<221> NAME/KEY: misc_feature
<222> LOCATION: (27)..(27)
<223> OTHER INFORMATION: red fluorescent dye attached to Adenine through
      Amino-modifier C6 dT linker

<400> SEQUENCE: 10
acatacatac atacatacau acataca                              27

<210> SEQ ID NO 11
<211> LENGTH: 26
<212> TYPE: DNA
<213> ORGANISM: Artificial Sequence
<220> FEATURE:
<223> OTHER INFORMATION: synthesized
<220> FEATURE:
<221> NAME/KEY: misc_feature
<222> LOCATION: (26)..(26)
<223> OTHER INFORMATION: red fluorescent dye attached to Thymine through
      Amino-modifier C6 dT linker

<400> SEQUENCE: 11
attgattgat tgattgatug attgat                               26
```

```
<210> SEQ ID NO 12
<211> LENGTH: 29
<212> TYPE: DNA
<213> ORGANISM: Artificial Sequence
<220> FEATURE:
<223> OTHER INFORMATION: synthesized
<220> FEATURE:
<221> NAME/KEY: misc_feature
<222> LOCATION: (29)..(29)
<223> OTHER INFORMATION: xanthene fluorophore attached to Adenine
      through Amino-modifier C6 dT linker

<400> SEQUENCE: 12
catctaggca tctaagcatc aaucttaca                                        29

<210> SEQ ID NO 13
<211> LENGTH: 27
<212> TYPE: DNA
<213> ORGANISM: Artificial Sequence
<220> FEATURE:
<223> OTHER INFORMATION: synthesized
<220> FEATURE:
<221> NAME/KEY: misc_feature
<222> LOCATION: (27)..(27)
<223> OTHER INFORMATION: xanthene fluorophore attached to Adenine
      through Amino-modifier C6 dT linker

<400> SEQUENCE: 13
acatacatac atacatacau acataca                                          27

<210> SEQ ID NO 14
<211> LENGTH: 26
<212> TYPE: DNA
<213> ORGANISM: Artificial Sequence
<220> FEATURE:
<223> OTHER INFORMATION: synthesized
<220> FEATURE:
<221> NAME/KEY: misc_feature
<222> LOCATION: (26)..(26)
<223> OTHER INFORMATION: xanthene fluorophore attached to Thymine
      through Amino-modifier C6 dT linker

<400> SEQUENCE: 14
attgattgat tgattgatug attgat                                           26

<210> SEQ ID NO 15
<211> LENGTH: 33
<212> TYPE: DNA
<213> ORGANISM: Artificial Sequence
<220> FEATURE:
<223> OTHER INFORMATION: synthesized
<220> FEATURE:
<221> NAME/KEY: misc_feature
<222> LOCATION: (33)..(33)
<223> OTHER INFORMATION: xanthene fluorophore attached to Adenine
      through Amino-modifier C6 dT linker

<400> SEQUENCE: 15 tttttacat acatacatac atacauacat aca                                    33

<210> SEQ ID NO 16
<211> LENGTH: 28
<212> TYPE: DNA
<213> ORGANISM: Artificial Sequence
<220> FEATURE:
<223> OTHER INFORMATION: synthesized

<400> SEQUENCE: 16
```
aatgatacgg cgaccaccga gauctaca                               28

<210> SEQ ID NO 17
<211> LENGTH: 28
<212> TYPE: DNA
<213> ORGANISM: Artificial Sequence
<220> FEATURE:
<223> OTHER INFORMATION: synthesized

<400> SEQUENCE: 17
aatgatacgg cgaccaccga gaucacac                               28

<210> SEQ ID NO 18
<211> LENGTH: 34
<212> TYPE: DNA
<213> ORGANISM: Artificial Sequence
<220> FEATURE:
<223> OTHER INFORMATION: synthesized

<400> SEQUENCE: 18 tttttaatg atacggcgac caccgagauc taca                         34

<210> SEQ ID NO 19
<211> LENGTH: 34
<212> TYPE: DNA
<213> ORGANISM: Artificial Sequence
<220> FEATURE:
<223> OTHER INFORMATION: synthesized

<400> SEQUENCE: 19 tttttaatg atacggcgac caccgagauc acac                         34

<210> SEQ ID NO 20
<211> LENGTH: 35
<212> TYPE: DNA
<213> ORGANISM: Artificial Sequence
<220> FEATURE:
<223> OTHER INFORMATION: sythesized

<400> SEQUENCE: 20 tttttaatg atacggcgac caccgagauc tacac                        35

<210> SEQ ID NO 21
<211> LENGTH: 34
<212> TYPE: DNA
<213> ORGANISM: Artificial Sequence
<220> FEATURE:
<223> OTHER INFORMATION: synthesized
<220> FEATURE:
<221> NAME/KEY: misc_feature
<222> LOCATION: (34)..(34)
<223> OTHER INFORMATION: xanthene fluorophore attached to adenine
      through Amino-modifier C6 dT linker

<400> SEQUENCE: 21 tttttaatg atacggcgac caccgagauc taca                         34

<210> SEQ ID NO 22
<211> LENGTH: 30
<212> TYPE: DNA
<213> ORGANISM: Artificial Sequence
<220> FEATURE:
<223> OTHER INFORMATION: synthesized
<220> FEATURE:
<221> NAME/KEY: misc_feature
<222> LOCATION: (30)..(30)
<223> OTHER INFORMATION: xanthene fluorophore attached to Cytosine
      through Amino-modifier C6 dT linker -continued

<400> SEQUENCE: 22 tttttttaatg atacggcgac caccgagauc                                          30

<210> SEQ ID NO 23
<211> LENGTH: 35
<212> TYPE: DNA
<213> ORGANISM: Artificial Sequence
<220> FEATURE:
<223> OTHER INFORMATION: synthesized
<220> FEATURE:
<221> NAME/KEY: misc_feature
<222> LOCATION: (35)..(35)
<223> OTHER INFORMATION: xanthene fluorophore attached to Cytosine
      through Amino-modifier C6 dT linker

<400> SEQUENCE: 23 tttttttaatg atacggcgac caccgagauc tacac                                    35

<210> SEQ ID NO 24
<211> LENGTH: 28
<212> TYPE: DNA
<213> ORGANISM: Artificial Sequence
<220> FEATURE:
<223> OTHER INFORMATION: synthesized
<220> FEATURE:
<221> NAME/KEY: misc_feature
<222> LOCATION: (28)..(28)
<223> OTHER INFORMATION: red fluorescent dye attached to adenine through
      Amino-modifier C6 dT linker

<400> SEQUENCE: 24
aatgatacgg cgaccaccga gauctaca                                             28

<210> SEQ ID NO 25
<211> LENGTH: 49
<212> TYPE: DNA
<213> ORGANISM: Artificial Sequence
<220> FEATURE:
<223> OTHER INFORMATION: synthesized
<220> FEATURE:
<221> NAME/KEY: misc_feature
<222> LOCATION: (1)..(20)
<223> OTHER INFORMATION: present or absent Thymine base
<220> FEATURE:
<221> NAME/KEY: misc_feature
<222> LOCATION: (49)..(49)
<223> OTHER INFORMATION: red fluorescent dye attached to adenine through
      Amino-modifier C6 dT linker

<400> SEQUENCE: 25
nnnnnnnnnn nnnnnnnnnn catctaggca tctaagcatc aaucttaca                      49

<210> SEQ ID NO 26
<211> LENGTH: 48
<212> TYPE: DNA
<213> ORGANISM: Artificial Sequence
<220> FEATURE:
<223> OTHER INFORMATION: synthesized
<220> FEATURE:
<221> NAME/KEY: misc_feature
<222> LOCATION: (1)..(20)
<223> OTHER INFORMATION: present or absent Thymine base
<220> FEATURE:
<221> NAME/KEY: misc_feature

```
<222> LOCATION: (48)..(48)
<223> OTHER INFORMATION: red fluorescent dye attached to adenine through
      Amino-modifier C6 dT linker

<400> SEQUENCE: 26
nnnnnnnnnn nnnnnnnnnn aatgatacgg cgaccaccga gauctaca          48
```